US009737358B2

(12) United States Patent
Beckman et al.

(10) Patent No.: US 9,737,358 B2
(45) Date of Patent: *Aug. 22, 2017

(54) HEAT MANAGEMENT CONFIGURATIONS FOR CONTROLLING HEAT DISSIPATION FROM ELECTROSURGICAL INSTRUMENTS

(71) Applicant: Ethicon Endo-Surgery, LLC, Guaynabo, PR (US)

(72) Inventors: Andrew T. Beckman, Cincinnati, OH (US); Bradley E. White, Lebanon, OH (US); Cory G. Kimball, Hamilton, OH (US); John F. Cummings, Madeira, OH (US); Al Mirel, Redwood City, CA (US); Christopher J. Schall, Mason, OH (US); Jeffrey L. Aldridge, Lebanon, OH (US); Timothy G. Dietz, Wayne, PA (US); David A. Witt, Maineville, OH (US); Mary E. Mootoo, Cincinnati, OH (US); Zhifan F. Huang, Mason, OH (US); Raymond M. Banks, Cupertino, CA (US); Tamara Widenhouse, Clarksville, OH (US); Frederick E. Shelton, IV, Hillsboro, OH (US); Jason L. Harris, Lebanon, OH (US); Jeffrey S. Swayze, West Chester, OH (US); Prasanna Malaviya, Mason, OH (US); Gregory W. Johnson, Milford, OH (US); Paul Guerra, Los Gatos, CA (US)

(73) Assignee: Ethicon LLC, Los Frailes Industrial Park, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/664,249

(22) Filed: Mar. 20, 2015

(65) Prior Publication Data

US 2015/0196352 A1 Jul. 16, 2015

Related U.S. Application Data

(63) Continuation of application No. 12/797,866, filed on Jun. 10, 2010, now Pat. No. 9,005,199.

(51) Int. Cl.
*A61B 18/14* (2006.01)
*A61B 17/32* (2006.01)
*A61B 18/00* (2006.01)

(52) U.S. Cl.
CPC ...... *A61B 18/1445* (2013.01); *A61B 18/1482* (2013.01); *A61B 17/32* (2013.01);
(Continued)

(58) Field of Classification Search
CPC ........ A61B 18/1445; A61B 2018/1452; A61B 2018/1455; A61B 2018/00029;
(Continued)

(56) References Cited

U.S. PATENT DOCUMENTS 2,366,274 A 1/1945 Luth et al.
2,458,152 A 1/1949 Eakins
(Continued)

FOREIGN PATENT DOCUMENTS

DE 10201569 A1 7/2003
EP 0340803 B1 8/1993
(Continued)

OTHER PUBLICATIONS

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
(Continued)

*Primary Examiner* — Thomas Giuliani

(57) ABSTRACT

In various embodiments, a surgical instrument is provided that may comprise an end effector for performing a surgical procedure on tissue, for example. The end effector may comprise at least one energy delivery surface and heat dissipation means for dissipating heat from at least a portion of the end effector. For example, in at least one embodiment, the end effector may comprise a first jaw, a second jaw, and a cutting member. The cutting member may comprise a
(Continued)

cutting surface and a body, which may define a cavity and at least one opening communicating with the cavity. A fluid may be moved through the cavity to and/or from the opening(s). Additionally, in at least one embodiment, a surgical instrument's end effector may comprise a first jaw, a second jaw, a cutting member, and at least one heat pipe. Various other heat dissipation means are also disclosed.

20 Claims, 19 Drawing Sheets

(52) U.S. Cl.
CPC ............... *A61B 2018/00005* (2013.01); *A61B 2018/00011* (2013.01); *A61B 2018/00017* (2013.01); *A61B 2018/00023* (2013.01); *A61B 2018/00029* (2013.01); *A61B 2018/00047* (2013.01); *A61B 2018/0063* (2013.01); *A61B 2018/00619* (2013.01); *A61B 2018/1412* (2013.01); *A61B 2018/1452* (2013.01); *A61B 2018/1455* (2013.01); *A61B 2018/1472* (2013.01); *A61B 2218/002* (2013.01)

(58) Field of Classification Search
CPC .... A61B 2018/1472; A61B 2018/1412; A61B 2018/00047; A61B 2018/00607; A61B 2018/0225
USPC .............................................. 606/50–52, 41
See application file for complete search history.

(56) References Cited

U.S. PATENT DOCUMENTS

| | | |
|---|---|---|
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,910,389 A | 3/1990 | Sherman et al. |
| 4,920,978 A | 5/1990 | Colvin |
| 4,936,842 A | 6/1990 | D'Amelio et al. |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,318,564 A | 6/1994 | Eggers |
| 5,318,589 A | 6/1994 | Lichtman |
| 5,330,471 A | 7/1994 | Eggers |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,542,916 A | 8/1996 | Hirsch et al. |
| 5,558,671 A | 9/1996 | Yates |
| 5,563,179 A | 10/1996 | Stone et al. |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,611,813 A | 3/1997 | Lichtman |
| 5,618,307 A | 4/1997 | Donlon et al. |
| 5,624,452 A | 4/1997 | Yates |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,713,896 A | 2/1998 | Nardella |
| 5,716,366 A | 2/1998 | Yates |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,836,909 A | 11/1998 | Cosmescu |

(56) References Cited

U.S. PATENT DOCUMENTS

| | | |
|---|---|---|
| 5,836,943 A | 11/1998 | Miller, III |
| 5,853,412 A | 12/1998 | Mayenberger |
| 5,876,401 A | 3/1999 | Schulze et al. |
| 5,880,668 A | 3/1999 | Hall |
| 5,891,142 A | 4/1999 | Eggers et al. |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,144,402 A | 11/2000 | Norsworthy et al. |
| 6,152,923 A | 11/2000 | Ryan |
| 6,174,309 B1 | 1/2001 | Wrublewski et al. |
| 6,206,876 B1 | 3/2001 | Levine et al. |
| 6,228,080 B1 | 5/2001 | Gines |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,702 B2 | 10/2002 | Schulze et al. |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |

(56) References Cited

U.S. PATENT DOCUMENTS

| | | |
|---|---|---|
| 7,494,501 B2 | 2/2009 | Ahlberg et al. |
| 7,498,080 B2 | 3/2009 | Tung et al. |
| 7,510,107 B2 | 3/2009 | Timm et al. |
| 7,513,025 B2 | 4/2009 | Fischer |
| 7,517,349 B2 | 4/2009 | Truckai et al. |
| 7,540,872 B2 | 6/2009 | Schechter et al. |
| 7,550,216 B2 | 6/2009 | Ofer et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,527 B2 | 5/2010 | Bouchier et al. |
| 7,722,607 B2 | 5/2010 | Dumbauld et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,819,872 B2 | 10/2010 | Johnson et al. |
| 7,832,408 B2 | 11/2010 | Shelton, IV et al. |
| 7,832,612 B2 | 11/2010 | Baxter, III et al. |
| 7,846,159 B2 | 12/2010 | Morrison et al. |
| 7,846,160 B2 | 12/2010 | Payne et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,058,771 B2 | 11/2011 | Giordano et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,221,415 B2 | 7/2012 | Francischelli |
| 8,241,235 B2 | 8/2012 | Kahler et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 * | 10/2012 | Kerr .................. A61B 18/1445 606/48 |
| 8,298,232 B2 | 10/2012 | Unger |
| 8,303,583 B2 | 11/2012 | Hosier et al. |
| 8,323,310 B2 | 12/2012 | Kingsley |
| 8,357,158 B2 | 1/2013 | McKenna et al. |
| 8,377,059 B2 | 2/2013 | Deville et al. |
| 8,397,971 B2 | 3/2013 | Yates et al. |
| 8,414,577 B2 | 4/2013 | Boudreaux et al. |
| 8,430,876 B2 | 4/2013 | Kappus et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,486,057 B2 | 7/2013 | Behnke, II |
| 8,496,682 B2 | 7/2013 | Guerra et al. |
| 8,535,311 B2 | 9/2013 | Schall |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| 8,613,383 B2 | 12/2013 | Beckman et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,647,350 B2 | 2/2014 | Mohan et al. |
| 8,663,222 B2 | 3/2014 | Anderson et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,404 B2 | 6/2014 | Boudreaux et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,834,466 B2 | 9/2014 | Cummings et al. |
| 8,834,518 B2 | 9/2014 | Faller et al. |
| 8,888,776 B2 | 11/2014 | Dietz et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,986,302 B2 | 3/2015 | Aldridge et al. |
| 9,005,199 B2 * | 4/2015 | Beckman ............ A61B 18/1482 606/52 |
| 9,011,437 B2 | 4/2015 | Woodruff et al. |
| 9,028,519 B2 | 5/2015 | Yates et al. |
| 9,044,243 B2 | 6/2015 | Johnson et al. |
| 9,149,324 B2 | 10/2015 | Huang et al. |
| 9,192,431 B2 | 11/2015 | Woodruff et al. |
| 2002/0022836 A1 | 2/2002 | Goble et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0212394 A1 * | 11/2003 | Pearson ............ A61B 18/1477 606/41 |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0092992 A1 | 5/2004 | Adams et al. |

(56) References Cited

U.S. PATENT DOCUMENTS

| | | |
|---|---|---|
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0221565 A1 | 9/2008 | Eder et al. |
| 2008/0262491 A1 | 10/2008 | Swoyer et al. |
| 2008/0269862 A1 | 10/2008 | Elmouelhi et al. |
| 2008/0272331 A1* | 11/2008 | Mohapatra ............... B01J 13/04 252/70 |
| 2008/0281315 A1 | 11/2008 | Gines |
| 2008/0294158 A1 | 11/2008 | Pappone et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0301605 A1 | 12/2011 | Horner |
| 2011/0306967 A1 | 12/2011 | Payne et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0150170 A1 | 6/2012 | Buysse et al. |
| 2012/0172859 A1 | 7/2012 | Condie et al. |
| 2012/0265196 A1 | 10/2012 | Turner et al. |
| 2013/0023875 A1 | 1/2013 | Harris et al. |
| 2013/0023925 A1 | 1/2013 | Mueller |
| 2013/0030433 A1 | 1/2013 | Heard |
| 2013/0079762 A1 | 3/2013 | Twomey et al. |
| 2013/0085496 A1 | 4/2013 | Unger et al. |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0131660 A1 | 5/2013 | Monson et al. |
| 2013/0253502 A1 | 9/2013 | Aronow et al. |
| 2013/0338661 A1 | 12/2013 | Behnke, II |
| 2014/0005680 A1 | 1/2014 | Shelton, IV et al. |
| 2014/0094801 A1 | 4/2014 | Boudreaux et al. |
| 2014/0148806 A1 | 5/2014 | Witt et al. |
| 2014/0194914 A1 | 7/2014 | Hunt et al. |
| 2014/0194915 A1 | 7/2014 | Johnson et al. |
| 2014/0257284 A1 | 9/2014 | Artale |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0066022 A1 | 3/2015 | Shelton, IV et al. |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133921 A1 | 5/2015 | Strobl et al. |
| 2015/0190189 A1 | 7/2015 | Yates et al. |
| 2015/0201953 A1 | 7/2015 | Strobl et al. |
| 2015/0230853 A1 | 8/2015 | Johnson et al. |
| 2015/0265347 A1 | 9/2015 | Yates et al. |
| 2015/0272602 A1 | 10/2015 | Boudreaux et al. |

(56) References Cited

U.S. PATENT DOCUMENTS

| | | |
|---|---|---|
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0051315 A1 | 2/2016 | Boudreaux |
| 2016/0051316 A1 | 2/2016 | Boudreaux |
| 2016/0051317 A1 | 2/2016 | Boudreaux |

FOREIGN PATENT DOCUMENTS

| | | | |
|---|---|---|---|
| EP | 0630612 A1 | 12/1994 | |
| EP | 0705571 A1 | 4/1996 | |
| EP | 0557806 B1 | 5/1998 | |
| EP | 0640317 B1 | 9/1999 | |
| EP | 0722696 B1 | 12/2002 | |
| EP | 1293172 B1 | 4/2006 | |
| EP | 1749479 A1 | 2/2007 | |
| EP | 1767157 A1 | 3/2007 | |
| EP | 1878399 A1 | 1/2008 | |
| EP | 1915953 A1 | 4/2008 | |
| EP | 1532933 B1 | 5/2008 | |
| EP | 1707143 B1 | 6/2008 | |
| EP | 1943957 A2 | 7/2008 | |
| EP | 1849424 B1 | 4/2009 | |
| EP | 2042117 A1 | 4/2009 | |
| EP | 2060238 A1 | 5/2009 | |
| EP | 1810625 B1 | 8/2009 | |
| EP | 2090238 A1 | 8/2009 | |
| EP | 2090256 A2 | 8/2009 | |
| EP | 2092905 A1 | 8/2009 | |
| EP | 2105104 A2 | 9/2009 | |
| EP | 1747761 B1 | 10/2009 | |
| EP | 1769766 B1 | 2/2010 | |
| EP | 2151204 A1 | 2/2010 | |
| EP | 2153791 A1 | 2/2010 | |
| EP | 2243439 A1 | 10/2010 | |
| EP | 1728475 B1 | 8/2011 | |
| EP | 2353518 A1 | 8/2011 | |
| EP | 2508143 B1 | 2/2014 | |
| GB | 2472216 A | 2/2011 | |
| JP | H 08-229050 A | 9/1996 | |
| JP | 2008-018226 A | 1/2008 | |
| WO | WO 81/03272 A1 | 11/1981 | |
| WO | WO 93/07817 A1 | 4/1993 | |
| WO | WO 93/22973 A1 | 11/1993 | |
| WO | WO 95/10978 A1 | 4/1995 | |
| WO | WO 96/35382 A1 | 11/1996 | |
| WO | WO 97/10764 A1 | 3/1997 | |
| WO | WO 98/00069 A1 | 1/1998 | |
| WO | WO 98/40020 A1 | 9/1998 | |
| WO | WO 98/57588 A1 | 12/1998 | |
| WO | WO 99/23960 A1 | 5/1999 | |
| WO | WO 99/40861 A1 | 8/1999 | |
| WO | WO 00/24330 A1 | 5/2000 | |
| WO | WO 00/24331 A1 | 5/2000 | |
| WO | WO 00/25691 A1 | 5/2000 | |
| WO | WO 01/28444 A1 | 4/2001 | |
| WO | WO 02/080797 A1 | 10/2002 | |
| WO | WO 03/001986 A2 | 1/2003 | |
| WO | WO 03/013374 A1 | 2/2003 | |
| WO | WO 03/020339 A2 | 3/2003 | |
| WO | WO 03/028541 A2 | 4/2003 | |
| WO | WO 03/030708 A2 | 4/2003 | |
| WO | WO 03/068046 A2 | 8/2003 | |
| WO | WO 2004/011037 A2 | 2/2004 | |
| WO | WO 2004/078051 A2 | 9/2004 | |
| WO | WO 2005/052959 A2 | 6/2005 | |
| WO | WO 2006/021269 A1 | 3/2006 | |
| WO | WO 2006/036706 A1 | 4/2006 | |
| WO | WO 2006/055166 A2 | 5/2006 | |
| WO | WO 2008/020964 A2 | 2/2008 | |
| WO | WO 2008/045348 A2 | 4/2008 | |
| WO | WO 2008/099529 A1 | 8/2008 | |
| WO | WO 2008/101356 A1 | 8/2008 | |
| WO | WO 2009/022614 A1 | 2/2009 | |
| WO | WO 2009/036818 A1 | 3/2009 | |
| WO | WO 2009/039179 A1 | 3/2009 | |
| WO | WO 2009/059741 A1 * | 5/2009 | ............ A61B 17/00 |
| WO | WO 2009/082477 A2 | 7/2009 | |
| WO | WO 2009/149234 A1 | 12/2009 | |
| WO | WO 2010/017266 A1 | 2/2010 | |
| WO | WO 2010/104755 A1 | 9/2010 | |
| WO | WO 2011/084768 A1 | 7/2011 | |
| WO | WO 2011/089717 A1 | 7/2011 | |
| WO | WO 2011/144911 A1 | 11/2011 | |
| WO | WO 2013/034629 A1 | 3/2013 | |
| WO | WO 2013/062978 A2 | 5/2013 | |
| WO | WO 2013/154157 A1 | 10/2013 | |

OTHER PUBLICATIONS

International Preliminary Report on Patentability for PCT/US2011/039715, Dec. 10, 2012 (11 pages).

International Search Report for PCT/US2011/039715, Dec. 6, 2011 (9 pages).

Written Opinion for PCT/US2011/039715, Dec. 6, 2011 (11 pages).

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

(56) References Cited

OTHER PUBLICATIONS

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, [Value Analysis Brief], LigaSure Advance™ Pistol Grip, dated Rev. Apr. 2010 (7 pages).

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

Covidien Brochure, The LigaSure Precise™ Instrument, dated Mar. 2011 (2 pages).

Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S_D027541.

Jang, J. et al. "Neuro-fuzzy and Soft Computing." Prentice Hall, 1997, pp. 13-89, 199-293, 335-393,453-496, 535-549.

Douglas, S.C. "Introduction to Adaptive Filter". Digital Signal Processing Handbook. Ed. Vijay K. Madisetti and Douglas B. Williams. Boca Raton: CRC Press LLC, 1999.

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

\* cited by examiner

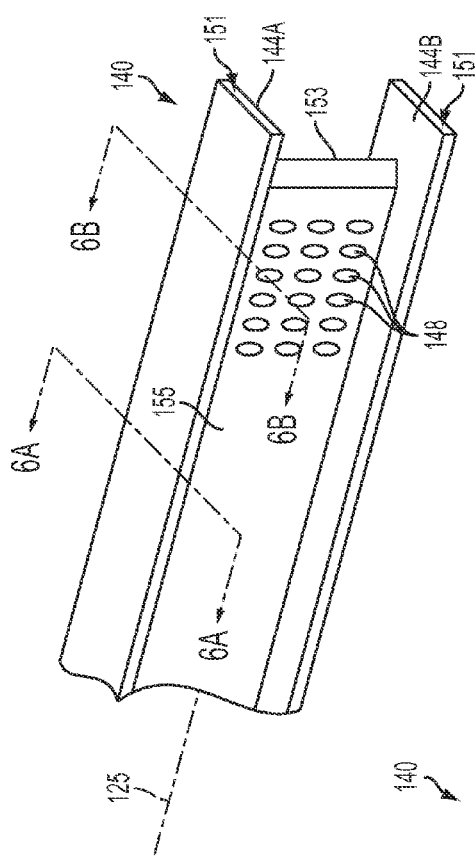
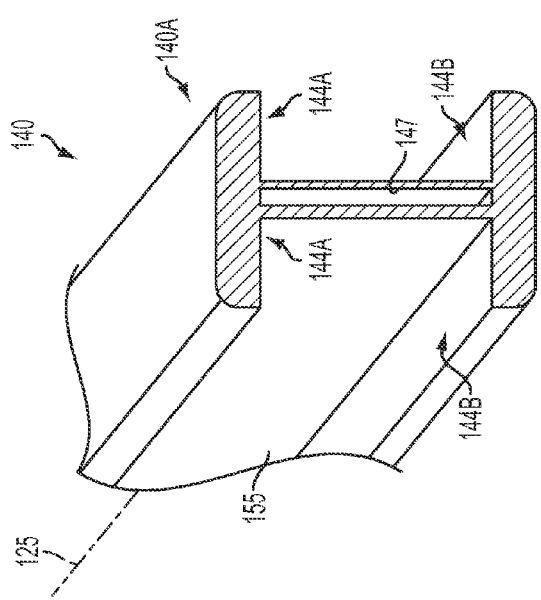
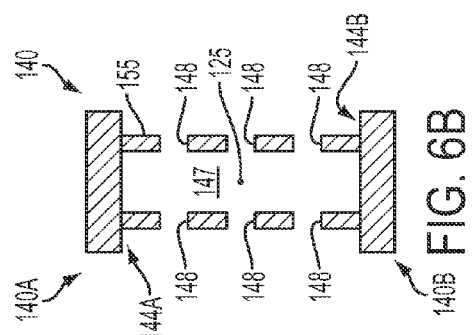

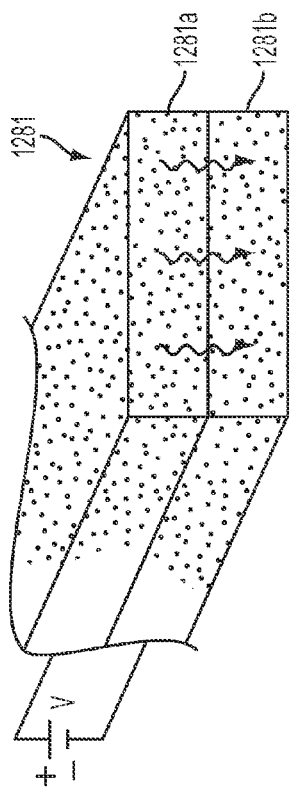
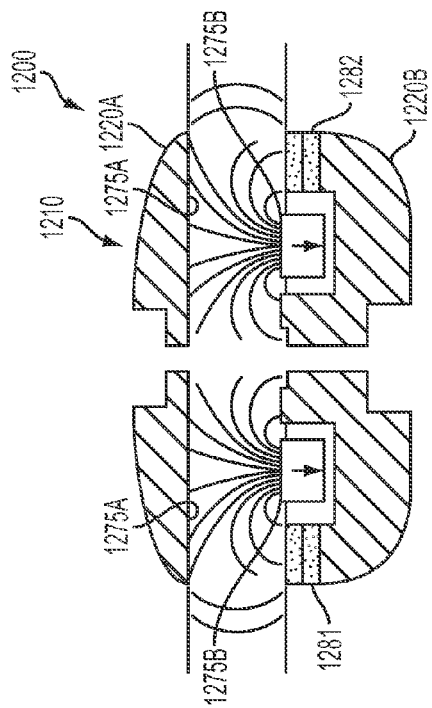
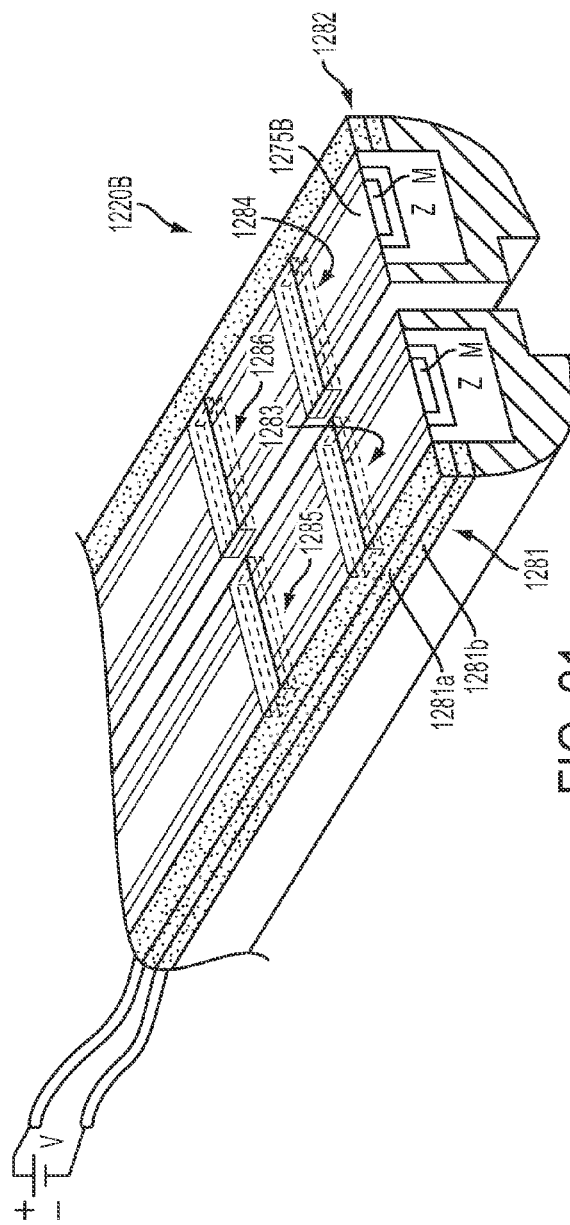

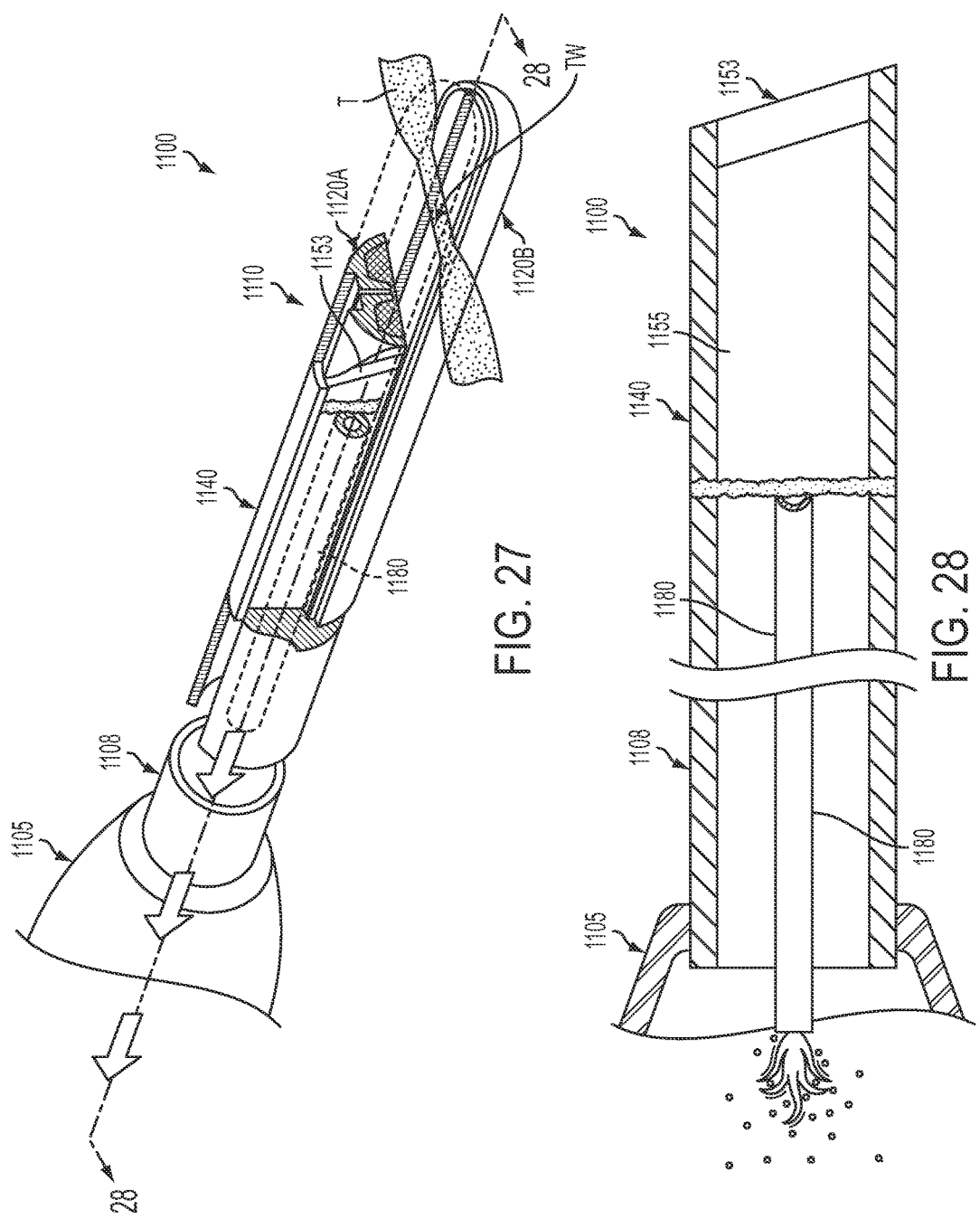

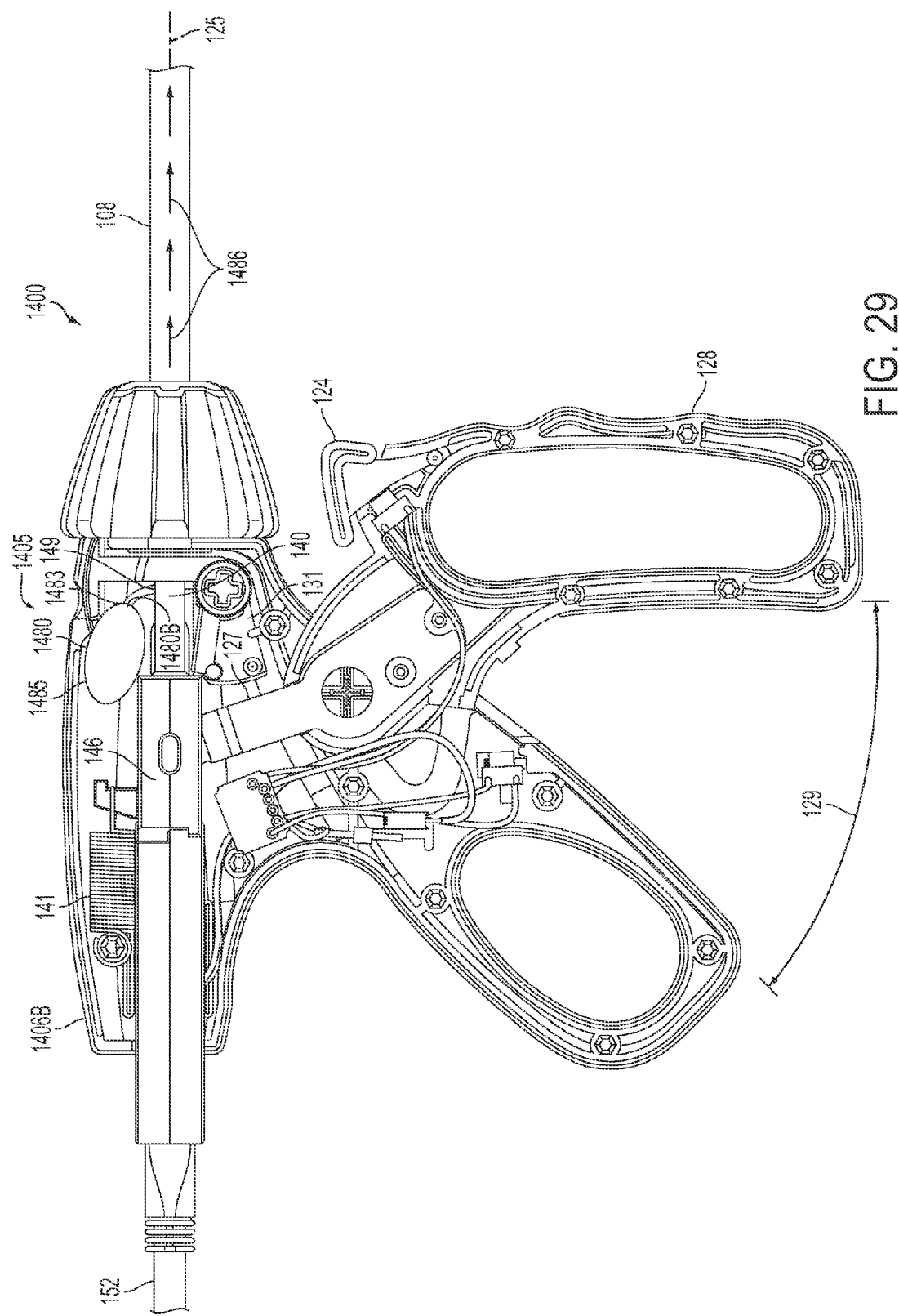

HEAT MANAGEMENT CONFIGURATIONS FOR CONTROLLING HEAT DISSIPATION FROM ELECTROSURGICAL INSTRUMENTS

CROSS-REFERENCE TO RELATED APPLICATION

The present application is a continuation application under 35 U.S.C. §120 of U.S. patent application Ser. No. 12/797,866, entitled HEAT MANAGEMENT CONFIGURATIONS FOR CONTROLLING HEAT DISSIPATION FROM ELECTROSURGICAL INSTRUMENTS, filed Jun. 10, 2010, now U.S. Pat. No. 9,005,199, the entire disclosure of which is incorporated by reference herein.

BACKGROUND

The present disclosure is directed to medical devices and methods, and, more particularly, to electrosurgical instruments and methods for sealing and transecting tissue.

In various circumstances, a surgical instrument can be configured to apply energy to tissue in order to treat and/or destroy the tissue. In certain circumstances, a surgical instrument can comprise one or more electrodes which can be positioned against and/or positioned relative to the tissue such that electrical current can flow from one electrode, through the tissue, and to the other electrode. The surgical instrument can comprise an electrical input, a supply conductor electrically coupled with the electrodes, and/or a return conductor which can be configured to allow current to flow from the electrical input, through the supply conductor, through the electrodes and the tissue, and then through the return conductor to an electrical output, for example. In various circumstances, heat can be generated by the current flowing through the tissue, wherein the heat can cause one or more hemostatic seals to form within the tissue and/or between tissues. Such embodiments may be particularly useful for sealing blood vessels, for example. The surgical instrument can also comprise a cutting member that can be moved relative to the tissue and the electrodes in order to transect the tissue.

By way of example, energy applied by a surgical instrument may be in the form of radio frequency ("RF") energy. RF energy is a form of electrical energy that may be in the frequency range of 300 kilohertz (kHz) to 1 megahertz (MHz). In application, RF surgical instruments transmit low frequency radio waves through electrodes, which cause ionic agitation, or friction, increasing the temperature of the tissue. Since a sharp boundary is created between the affected tissue and that surrounding it, surgeons can operate with a high level of precision and control, without much sacrifice to the adjacent normal tissue. The low operating temperatures of RF energy enables surgeons to remove, shrink or sculpt soft tissue while simultaneously sealing blood vessels. RF energy works particularly well on connective tissue, which is primarily comprised of collagen and shrinks when contacted by heat.

Further, in various open and laparoscopic surgeries, it may be necessary to coagulate, seal or fuse tissues. One means of sealing tissue relies upon the application of electrical energy to tissue captured within an end effector of a surgical instrument in order to cause thermal effects within the tissue. Various mono-polar and bi-polar RF jaw structures have been developed for such purposes. In general, the delivery of RF energy to the captured tissue elevates the temperature of the tissue and, as a result, the energy can at least partially denature proteins within the tissue. Such proteins, such as collagen, for example, may be denatured into a proteinaceous amalgam that intermixes and fuses, or "welds," together as the proteins renature. As the treated region heals over time, this biological "weld" may be reabsorbed by the body's wound healing process.

In certain arrangements of a bi-polar radiofrequency (RF) jaw, the surgical instrument can comprise opposing first and second jaws, wherein the face of each jaw can comprise an electrode. In use, the tissue can be captured between the jaw faces such that electrical current can flow between the electrodes in the opposing jaws and through the tissue positioned therebetween. Such instruments may have to seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. With particular regard to sealing large diameter blood vessels, for example, such applications may require a high strength tissue weld immediately post-treatment.

The foregoing discussion is intended only to illustrate the present field and should not be taken as a disavowal of claim scope.

SUMMARY

In various embodiments, a surgical instrument is provided. In at least one embodiment, the surgical instrument can comprise an end effector comprising a first jaw, a second jaw, and a cutting member. In these embodiments, the first jaw and the second jaw can be operably coupled together. Additionally, in these embodiments, the cutting member can be configured to translate with respect to the first jaw. Further, in these embodiments, the cutting member can comprise a cutting surface and a body. Moreover, in these embodiments, the body can define a cavity and at least one opening communicating with the cavity.

In at least one embodiment, a surgical instrument is provided that can comprise an end effector comprising a first jaw, a second jaw, a cutting member, and at least one heat pipe. In these embodiments, the first jaw can comprise an energy delivery surface and define a channel. Additionally, in these embodiments, the first jaw and the second jaw can be operably coupled together. Further, the cutting member can be configured to translate with respect to the first jaw.

In at least one embodiment, a surgical instrument is provided that can comprise an end effector. In these embodiments, the end effector can comprise at least one energy delivery surface and heat dissipation means for dissipating heat from at least a portion of the end effector.

The foregoing discussion should not be taken as a disavowal of claim scope.

FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 5 is a perspective view of a portion of a cutting member of the surgical instrument of FIG. 1; the cutting member is shown at least partially shaped like an I-beam.

FIG. 6A is a perspective sectional view of a portion of the cutting member of the surgical instrument of FIG. 1, taken along line 6A-6A in FIG. 5.

FIG. 6B is a cross-sectional view of the cutting member of the surgical instrument of FIG. 1, taken along line 6B-6B in FIG. 5.

FIG. 19 is a cross-sectional view of an end effector of a surgical instrument according to a non-limiting embodiment.

FIG. 20 is a perspective sectional view of a portion of a Peltier device of the end effector of FIG. 19.

FIG. 21 is a perspective sectional view of a portion of a jaw of the end effector of FIG. 19.

FIG. 27 is a perspective, partial-sectional view of various components of a surgical instrument according to a non-limiting embodiment.

FIG. 28 is a side cross-sectional view of a portion of the surgical instrument of FIG. 27, taken along line 28-28; jaws of the surgical instrument are omitted for clarity.

FIG. 29 is a side view of a handle of a surgical instrument according to a non-limiting embodiment; half of a handle body of the surgical instrument is removed to illustrate some of the components therein.

Figure 1:
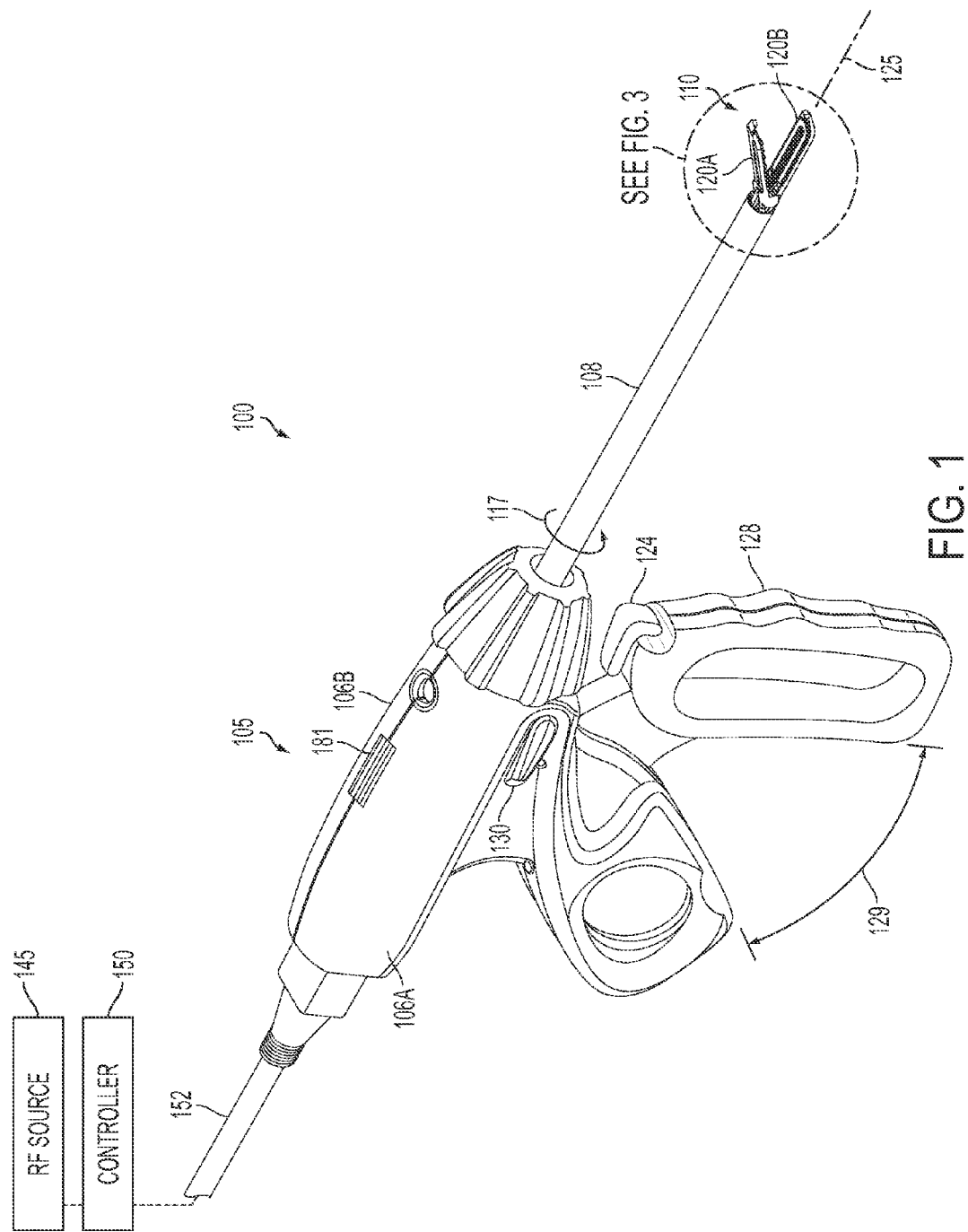
FIG. 1 is a perspective view of a surgical instrument according to a non-limiting embodiment.

Corresponding reference characters indicate corresponding parts throughout the several views. The exemplifications set out herein illustrate various embodiments, in one or more forms, and such exemplifications are not to be construed as limiting the scope of the claims in any manner.

DETAILED DESCRIPTION

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments,"

"in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located farthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

The following United States patent applications, filed on Jun. 10, 2010, are also hereby incorporated by reference herein:

U.S. patent application Ser. No. 12/797,844, entitled ELECTROSURGICAL INSTRUMENT COMPRISING SEQUENTIALLY ACTIVATED ELECTRODES, now U.S. Pat. No. 8,764,747;

U.S. patent application Ser. No. 12/797,853, entitled ELECTROSURGICAL INSTRUMENT EMPLOYING A THERMAL MANAGEMENT SYSTEM, now U.S. Pat. No. 8,753,338; and U.S. patent application Ser. No. 12/797,861, entitled COOLING CONFIGURATIONS FOR ELECTROSURGICAL INSTRUMENTS, now U.S. Patent Application Publication No. 2011-0306967.

Various embodiments of systems and methods relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

A surgical instrument can be configured to supply energy, such as electrical energy, ultrasonic energy, and/or heat energy, for example, to the tissue of a patient. For example, various embodiments disclosed herein provide electrosurgical jaw structures adapted for transecting captured tissue between the jaws and for contemporaneously welding or sealing the captured tissue margins with controlled application of RF energy. In more detail, in various embodiments, referring now to FIG. 1, an electrosurgical instrument 100 is shown. Surgical or electrosurgical instrument 100 can comprise a proximal handle 105, a distal working end or end effector 110 and an introducer or elongate shaft 108 disposed in-between. End effector 110 may comprise a set of openable-closeable jaws with straight or curved jaws—an upper first jaw 120A and a lower second jaw 120B. First jaw 120A and second jaw 120B may each comprise an elongate slot or channel 142A and 142B (see FIG. 3), respectively, disposed outwardly along their respective middle portions. First jaw 120A and second jaw 120B may be coupled to an electrical source 145 and a controller 150 through electrical leads in cable 152. Controller 150 may be used to activate electrical source 145. In various embodiments, the electrical source 145 may comprise an RF source, an ultrasonic source, a direct current source, and/or any other suitable type of electrical energy source, for example.

Figure 2:
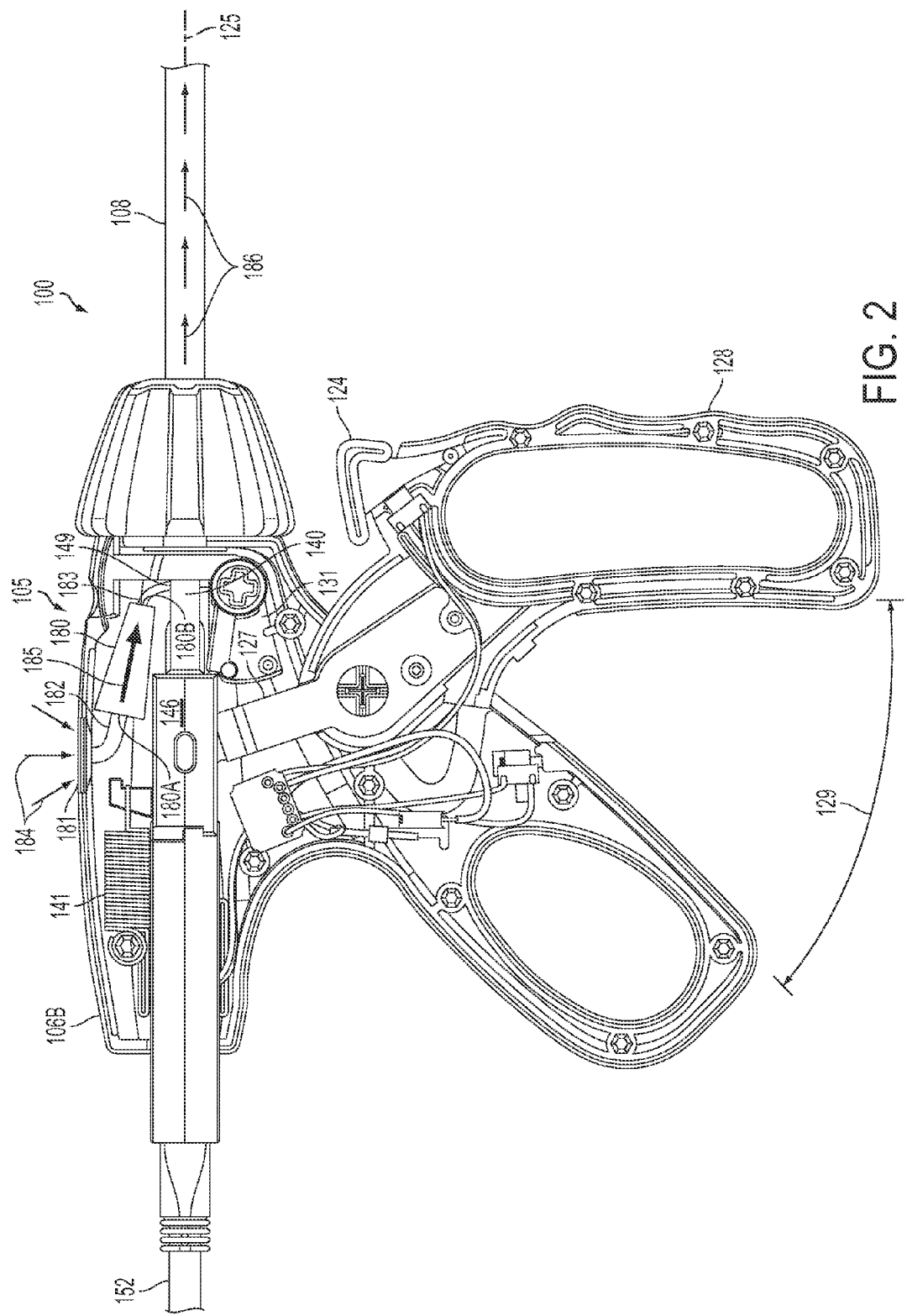
FIG. 2 is a side view of a handle of the surgical instrument of FIG. 1 with a half of a handle body removed to illustrate some of the components therein.

Moving now to FIG. 2, a side view of the handle 105 is shown with half of a first handle body 106A (see FIG. 1) removed to illustrate some of the components within second handle body 106B. Handle 105 may comprise a lever arm 128 which may be pulled along a path 129. Lever arm 128 may be coupled to a movable cutting member 140 disposed within elongate shaft 108 by a shuttle 146 operably engaged to an extension 127 of lever arm 128. The shuttle 146 may further be connected to a biasing device, such as spring 141, which may also be connected to the second handle body 106B, to bias the shuttle 146 and thus the cutting member 140 in a proximal direction, thereby urging the jaws 120A and 120B to an open position as seen in FIG. 1. Also, referring to FIGS. 1 and 2, a locking member 131 (see FIG. 2) may be moved by a locking switch 130 (see FIG. 1) between a locked position, where the shuttle 146 is substantially prevented from moving distally as illustrated, and an unlocked position, where the shuttle 146 may be allowed to freely move in the distal direction, toward the elongate shaft 108. The handle 105 can be any type of pistol-grip or other type of handle known in the art that is configured to carry actuator levers, triggers or sliders for actuating the first jaw 120A and second jaw 120B. Elongate shaft 108 may have a cylindrical or rectangular cross-section and can comprise a thin-wall tubular sleeve that extends from handle 105. Elongate shaft 108 may include a bore extending therethrough for carrying actuator mechanisms, for example, cutting member 140, for actuating the jaws and for carrying electrical leads for delivery of electrical energy to electrosurgical components of end effector 110.

End effector 110 may be adapted for capturing, welding or sealing, and transecting tissue. First jaw 120A and second jaw 120B may close to thereby capture or engage tissue about a longitudinal axis 125 defined by cutting member 140. First jaw 120A and second jaw 120B may also apply compression to the tissue. Elongate shaft 108, along with first jaw 120A and second jaw 120B, can be rotated a full 360° degrees, as shown by arrow 117, relative to handle 105 through, for example, a rotary triple contact. First jaw 120A and second jaw 120B can remain openable and/or closeable while rotated.

Figure 3:
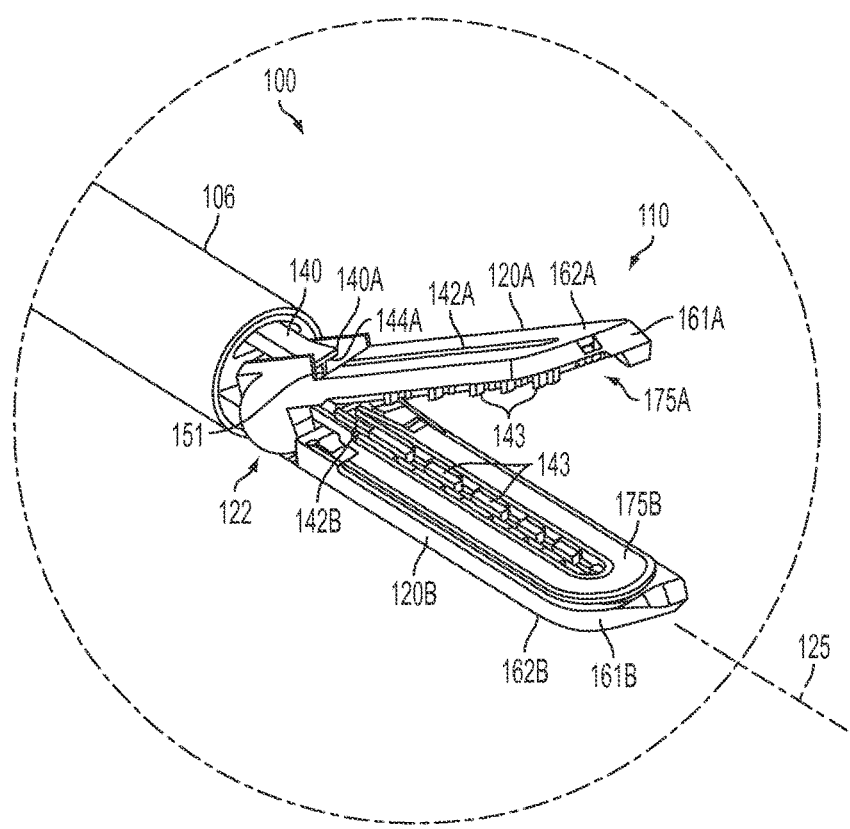
FIG. 3 is a perspective view of an end effector of the surgical instrument of FIG. 1 illustrated in an open configuration; the distal end of a cutting member is illustrated in a retracted position.
Figure 4:
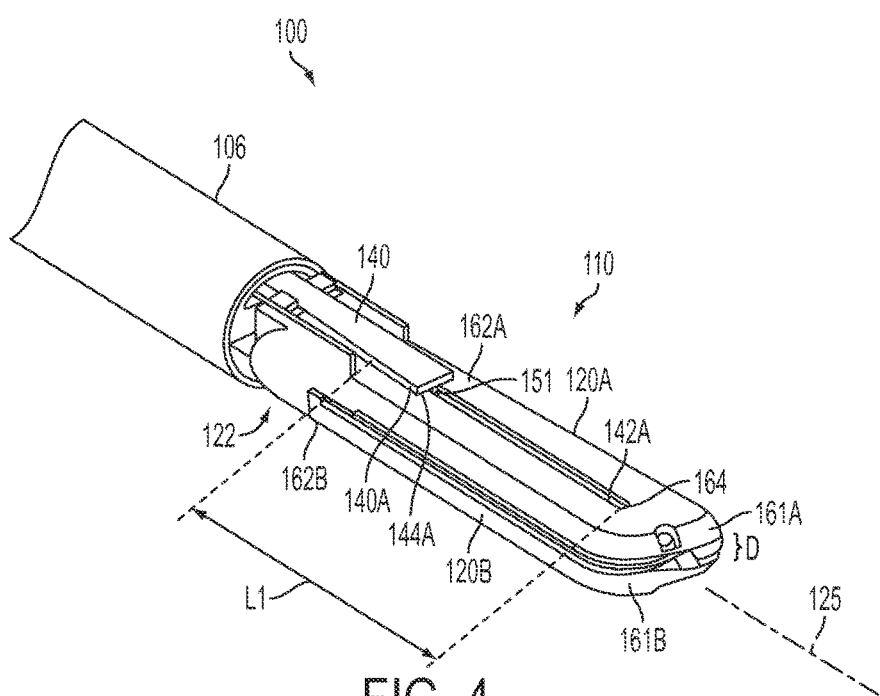
FIG. 4 is a perspective view of the end effector of the surgical instrument of FIG. 1 illustrated in a closed configuration; the distal end of the cutting member is illustrated in a partially advanced position.

FIGS. 3 and 4 illustrate perspective views of end effector 110. FIG. 3 shows end effector 110 in an open configuration and FIG. 4 shows end effector 110 in a closed configuration. As noted above, the end effector 110 may comprise the upper first jaw 120A and the lower second jaw 120B. Further, the first jaw 120A and second jaw 120B may each have tissue-gripping elements, such as teeth 143, disposed on the inner portions of first jaw 120A and second jaw 120B. First jaw 120A may comprise an upper first jaw body 161A with an upper first outward-facing surface 162A and an upper first energy delivery surface 175A of a first electrode, for example. Second jaw 120B may comprise a lower second jaw body 161B with a lower second outward-facing surface 162B and a lower second energy delivery surface 175B of a second electrode, for example. First energy delivery surface 175A and second energy delivery surface 175B may both extend in a "U" shape about the distal end of end effector 110. Additionally, in at least one embodiment, one or both electrodes may each comprise a segmented electrode or electrodes as described in U.S. patent application Ser. No. 12/797,844, entitled ELECTROSURGICAL INSTRUMENT COMPRISING SEQUENTIALLY ACTIVATED ELECTRODE, now U.S. Pat. No. 8,764,747, filed on Jun. 10, 2010 and incorporated by reference herein.

Referring briefly now to FIGS. 5-6A, a portion of cutting member 140 is shown. The lever arm 128 of handle 105, see FIG. 2, may be adapted to actuate cutting member 140 which also functions as a jaw-closing mechanism. For example, cutting member 140 may be urged distally as lever arm 128 is pulled proximally along path 129 via shuttle 146, seen in FIG. 2 and discussed above. The cutting member 140 may comprise one or several pieces, but in any event, may be movable or translatable with respect to the elongate shaft 108 and/or jaws 120A, 120B. Also, in at least one embodiment, the cutting member 140 may be made of 17-4 precipitation hardened stainless steel. The distal end of cutting member 140 may comprise a flanged "I"-beam configured to slide within channels 142A and 142B in jaws 120A and 120B. Cutting member 140 may slide within channels 142A, 142B to open and close first jaw 120A and second jaw 120B. The distal end of cutting member 140 may also comprise upper flange or "c"-shaped portion 140A and lower flange or "c"-shaped portion 140B. The flanges 140A and 140B respectively define inner cam surfaces 144A and 144B for engaging outward facing surfaces of first jaw 120A and second jaw 120B. The opening-closing of jaws 120A and 120B can apply very high compressive forces on tissue using cam mechanisms which may include reciprocating "I-beam" cutting member 140 and the outward facing surfaces 162A, 162B of jaws 120A, 120B.

More specifically, referring now to FIGS. 3-5, collectively, inner cam surfaces 144A and 144B of the distal end of cutting member 140 may be adapted to slidably engage first outward-facing surface 162A and second outward-facing surface 162B of first jaw 120A and second jaw 120B, respectively. Channel 142A within first jaw 120A and channel 142B within second jaw 120B may be sized and configured to accommodate the movement of cutting member 140, which may comprise a tissue-cutting element, for example, a sharp distal edge and/or surface 153 (see FIG. 5). FIG. 4, for example, shows the distal end of cutting member 140 advanced at least partially through channels 142A and 142B (see FIG. 3). The advancement of cutting member 140 can close end effector 110 from the open configuration shown in FIG. 3. The cutting member 140 may move or translate along the channel 142A between a retracted position and a fully advanced position. The retracted position can be seen in FIG. 3, where the jaws 120A, 120B are in an open position and a distal end 151 of the cutting member 140 is positioned proximal to the upper outward-facing surface 162A. The fully advanced position, while not shown, may occur when the distal end 151 of the cutting member 140 is advanced to a distal end 164 of channel 142A and the jaws are in a closed position, see FIG. 4. In the closed position shown by FIG. 4, upper first jaw 120A and lower second jaw 120B define a gap or dimension D between the first energy delivery surface 175A and second energy delivery surface 175B of first jaw 120A and second jaw 120B, respectively. Dimension D equals from about 0.0005" to about 0.005" and preferably between about 0.001" to about 0.002". Also, the edges of first energy delivery surface 175A and second energy delivery surface 175B may be rounded to prevent the dissection of tissue.

Referring now to FIGS. 1 and 3, end effector 110 may be coupled to electrical source 145 and controller 150. First energy delivery surface 175A and second energy delivery surface 175B may likewise each be coupled to electrical source 145 and controller 150. First energy delivery surface 175A and second energy delivery surface 175B may be configured to contact tissue and delivery electrosurgical energy to engaged tissue which is adapted to seal or weld the tissue. Controller 150 can regulate the electrical energy delivered by electrical source 145 which in turn delivers electrosurgical energy to first energy-delivery surface 175A and second energy-delivery surface 175B. The energy delivery may be initiated by an activation button 124 operably engaged with lever arm 128 and in electrical communication with controller 150 via cable 152. As mentioned above, the electrosurgical energy delivered by electrical source 145 may comprise radiofrequency (RF) energy. Further, the opposing first and second energy delivery surfaces 175A and 175B may carry variable resistive positive temperature coefficient (PTC) bodies that are coupled to electrical source 145 and controller 150. Additional details regarding electrosurgical end effectors, jaw closing mechanisms, and electrosurgical energy-delivery surfaces are described in the following U.S. patents and published patent applications, all of which are incorporated herein in their entirety by reference and made a part of this specification: U.S. Pat. Nos. 7,381,209; 7,311,709; 7,220,951; 7,189,233; 7,186,253; 7,125,409; 7,112,201; 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506.

In various embodiments, it may be desirable to dissipate heat from an end effector such that when energy is delivered to the end effector, as described above with respect to end effector 110, for instance, the likelihood that tissue contacting the end effector will be unintentionally thermally altered by the end effector may be reduced or eliminated. Additionally, dissipating heat from the end effector can lead to cooling the sealed area of tissue more quickly which may produce stronger tissue welds. Further, cooling the tissue and/or at least a portion of the end effector after welding the tissue, as discussed above, may minimize the amount of thermal energy spread into and/or through tissue adjacent to the desired seal area. Accordingly, in at least one embodiment and referring again to FIG. 1, a surgical instrument, such as surgical instrument 100 described above, may be configured to dissipate heat from an end effector by extracting heat or depositing a cooling medium to the target tissue and/or end effector. The surgical instrument 100 may comprise an end effector 110 that may also include at least one energy delivery surface, such as first and/or second energy delivery surfaces 175A and 175B (see FIG. 3). Additionally, in various embodiments, referring to FIG. 2, the surgical instrument 100 may comprise a pump, such as pump 180, for example, that is configured to cause a fluid to move into at least a portion of the end effector 110. More specifically, in at least one exemplary embodiment, referring now to FIGS. 1-2, a surgical instrument 100 may be provided that comprises a pump 180 operably coupled to a handle 105. FIG. 2 shows the first handle body removed to show the components of surgical instrument 100 associated with and/or within handle 105. As illustrated, the pump 180 may be coupled to part of the handle body, such as second handle body 106B. However, while pump 180 is shown located within handle 105, the pump 180 may alternatively be positioned external to the handle 105. In any event, the pump 180 may be configured to cause a fluid to move through the cutting member 140 and into at least a portion of the end effector 110. In at least one embodiment, the fluid may be a gas, such as air, for example. Alternatively, as discussed below, the fluid may be a liquid, such as water, distilled water, and/or saline solution, for example.

In more detail, referring still to FIGS. 1-2, the handle 105 may additionally comprise a fluid port 181 located on the body. The fluid port 181 may comprise a vent, for example, through which air from outside the instrument may pass. Additionally, in at least one embodiment, the fluid port 181 may comprise a filter, such as a HEPA air filter, to purify the air passing therethrough. The pump 180 may comprise an inlet 180A and an outlet 180B for the fluid to enter and exit the pump 180, respectively. In at least one embodiment, the inlet 180A may be coupled to the fluid port 181 via first tubing 182 and the outlet 180B may be coupled to the cutting member 140 by second tubing 183 at a proximal hole 149 of the cutting member 140.

In at least one embodiment, referring to FIG. 5, the cutting member 140 may comprise a body 155 and a cutting surface 153 that may be located at a distal portion of the cutting member 140. Referring now also to FIGS. 6A and 6B, the body 155 may define a cavity 147 therein and at least one opening, such as openings 148, for example. As shown, the cavity 147 may lie along the longitudinal axis 125 of the cutting member. Alternatively, although not shown in FIGS. 6A-6B, the cavity may be offset from the longitudinal axis 125. Additionally, as illustrated, there may be at least two or more openings 148. As can be seen in FIG. 6B, one or more of the openings 148 may communicate with the cavity 147 such that a fluid, may pass therethrough. In at least one embodiment, the openings 148 may be positioned proximal to the cutting surface 153. In other words, in various embodiments, taking the instrument 100 as a whole, the cutting member opening or openings 148 may be positioned between the handle 105 (FIG. 1) and the cutting surface 153 (FIG. 5). Further, in at least one embodiment, the opening or openings 148 may be positioned near the cutting surface 153 such that the openings 148 are configured to dissipate heat from tissue immediately after the tissue is cut by cutting surface 153. Additionally, although not illustrated, the proximal hole 149 in cutting member 140 may communicate with the cavity 147 such that fluid flowing from second tubing 183 and into the cutting member 140 may pass through the cavity 147 and out openings 148 to effectuate heat dissipation from the cut tissue and/or end effector 110. Accordingly, the cavity 147 may partially reside within the handle 105 to a distal end of the elongate shaft 108 and/or into end effector 110.

In use, the surgical instrument 100, may function as follows. In at least one embodiment, referring to FIGS. 1-2, when activation button 124 is pressed to supply energy to the end effector 110, as discussed above, the pump 180 may simultaneously or shortly thereafter activate. In such embodiments, the pump 180 may be connected to the activation button 124 by at least one electrical conductor (not shown), such as an electrical lead, insulated wire, and/or copper wire, for example. Accordingly, the button 124 may be configured to be moved between a first and a second position where the second position completes an electrical circuit such that current may flow from a power source outside the instrument, such as that associated with controller 150 and/or electrical source 145, for example, to the pump 180. Thus, in at least one embodiment, when the button 124 is depressed to the second position, electrical current may flow from the electrical source 145, for example, through the electrical conductors (not shown), to the pump 180. The pump 180 may thereby activate and begin to draw air, designated by arrows 184, into fluid port 181, through first tubing 182 and into pump 180 via inlet 180A. The pump 180 may continue to force the air, designated by arrow 185, out outlet 180B, into second tubing 183 and into the cutting member 140 via proximal hole 149. The air, designated by arrows 186, may then travel in a distal direction through the cavity 147 of the cutting member 140, through the elongate shaft 108, and toward the end effector 110. The air may thereafter be forced into at least a portion of the end effector 110. In at least one embodiment, the air may enter the space between jaws 120A and 120B, thereby allowing for the energy delivery surfaces 175A and 175B and any tissue between the jaws 120A and 120B to be subsequently cooled.

While the pump 180 may be configured to operate during a surgical procedure by being activated at or at about the same time as energy is delivered to surfaces 175A and/or 175B, the pump 180 may be configured to be selectively activated independently of the energy delivery activation button's use. Referring to FIG. 2, in at least one embodiment, the pump may alternatively be coupled to a control button (not shown) on the exterior of the handle 105. In such embodiments, the pump 180 may be activated before, during, and/or after a surgical procedure by pressing the control button, thereby allowing for selective cooling of the end effector 110 (see FIG. 1) before, during, and/or after a surgical operation. Alternatively, the pump may be activated by the controller 150 during a predetermined time within the treatment cycle, for example.

As discussed above, a surgical instrument may comprise a pump that is configured to cause a fluid to move over at least a portion of an end effector as described above, for example, by forcing or pushing a fluid, such as a gas, like air, for example, in a distal direction into at least a portion of the end effector. Alternatively, in various embodiments, a surgical instrument may comprise a pump that is configured to force or draw a fluid in a proximal direction over part of the end effector. In other words, a pump may be configured to function like a vacuum and draw one or more fluids into the end effector, for example. Accordingly, in at least one embodiment, referring to FIGS. 1, 2, and 5-6B, the pump 180 described above may be reversed such that, when the pump is activated, it functions as a vacuum. In such embodiments, air, carbon dioxide, or steam, for example, may be drawn into cutting member openings 148, through the cutting member cavity 147, out proximal hole 149, into pump 180, and then out fluid port 181, which may serve an exhaust vent. Accordingly, heated substances, such as air, carbon dioxide, and steam, for example, may be drawn from the end effector 110 and/or target tissue to remove the heated substance(s) therefrom, thereby cooling or dissipating heat from the end effector 110 and/or target tissue.

Figure 7:
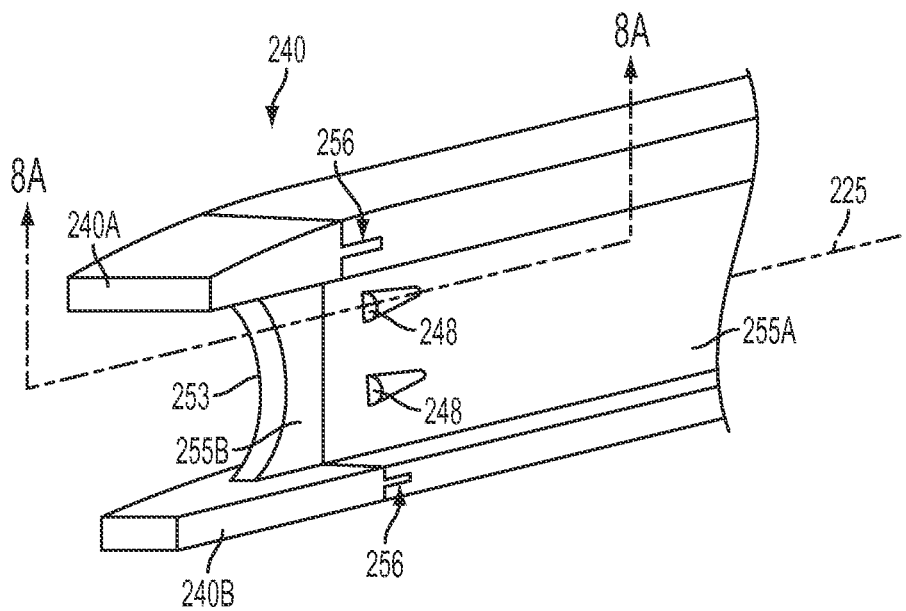
FIG. 7 is a perspective view of a portion of a cutting member of a surgical instrument according to a non-limiting embodiment.
Figure 8A:
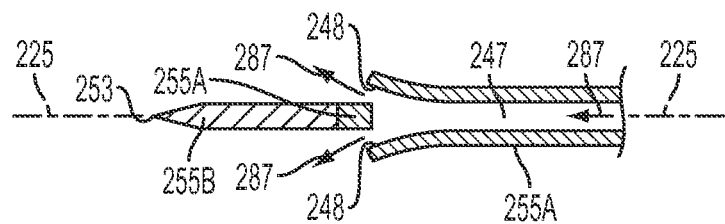
FIG. 8A is a cross-sectional view of the cutting member of FIG. 7 taken along line 8A-8A.

In various embodiments, different configurations of the cutting member 140, cavity 147, and/or opening(s) 148 may be employed to dissipate heat from the end effector 110 and/or target tissue. For example, as seen in FIGS. 5 and 6B, the cutting member 140 may define a longitudinal axis 125 and the opening(s) 148 may define a plane that is parallel to the longitudinal axis 125. In other words, the openings 148 may project to the sides of the cutting member 140. However, the opening or openings of a cutting member may be oriented differently. For example, referring now to FIGS. 7 and 8A, in at least one embodiment, a cutting member 240, similar in some respects to cutting member 140, may comprise a cutting surface 253 and a body including a distal body portion 255B (discussed in more detail below) and a proximal body portion 255A. The cutting surface 253 may be a part of and/or positioned on distal body portion 255B. The proximal body portion 255A may define a cavity 247 and openings 248 may communicate with the cavity 247. Further, the cutting member 240 may define a longitudinal axis 225 and the opening or openings 248 may define a plane that intersects the longitudinal axis 225. In other words, the openings may project proximally or distally with respect to the cutting surface 253 of the cutting member 240. As illustrated in FIGS. 7 and 8A, the openings 248 project distally, towards the cutting surface 253. Further, arrows 287 illustrate a potential fluid flow path for a fluid flowing through the cutting member's cavity 247 and out openings 248, for example.

Additional heat may be dissipated from the end effector 110 (FIG. 1) and/or the target tissue by using a cutting member, such as cutting member 240, for example, that comprises two materials. For example, referring to FIG. 7, the cutting member's proximal body portion 255A may be made from a plastic, whereas the cutting member's distal body portion 255B may be made from a metal, such as steel, for example. In at least one embodiment, the distal body portion 255B may be coupled to the proximal body portion 255A at one or more tongue-in-groove connections 256. In such embodiments, owing to the material disparity and the inability of plastic to efficiently conduct heat, any heated substance passed through the cutting member's proximal body portion 255A may not conduct heat as effectively as the distal portion 255B, thereby preventing or resisting components of the surgical instrument 100 (FIG. 1), including end effector 110 and shaft 108, for example, from heating up when a heat substance is passed through the cutting member 240. Such embodiments may be particularly useful when the pump 180 (FIG. 2) is used as a vacuum to draw heated air and/or steam through the cutting member 240, for example.

Figure 8B:
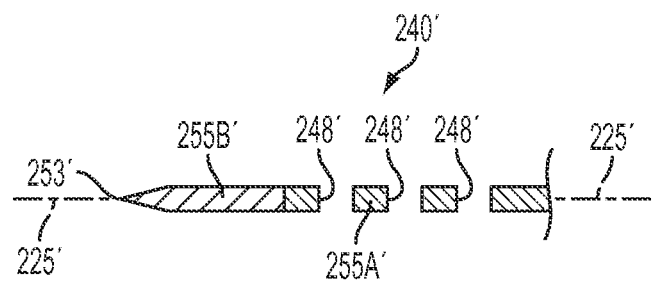
FIG. 8B is a cross-sectional view of a portion of a cutting member of a surgical instrument according to a non-limiting embodiment.
Figure 8C:
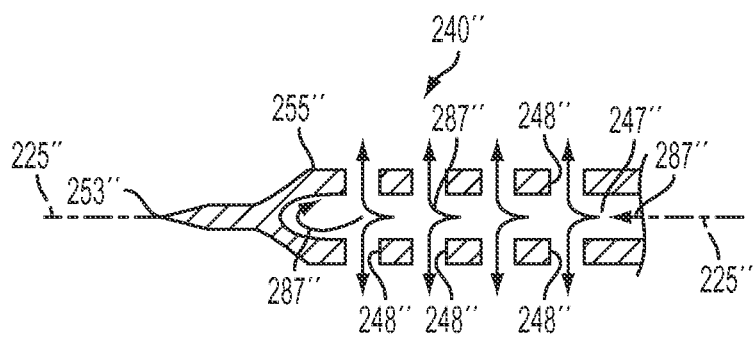
FIG. 8C is a cross-sectional view of a portion of a cutting member of a surgical instrument according to a non-limiting embodiment.
Figure 8D:
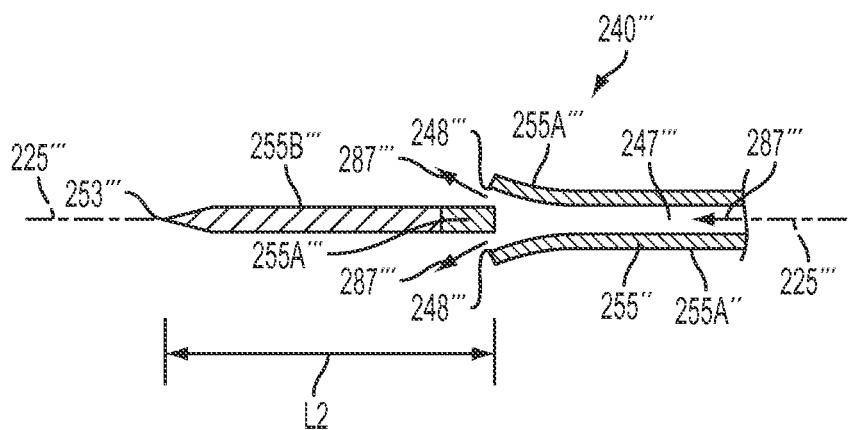
FIG. 8D is a cross-sectional view of a portion of a cutting member of a surgical instrument according to a non-limiting embodiment.

Additional exemplary configurations of a cutting member, similar in some respects to cutting member 140 described above, are shown in FIGS. 8B-8D. FIGS. 8B, 8C, and 8D illustrate cutting members 240', 240", and 240'", respectively, and are taken along a similar cross-section line as line 8A-8A seen in FIG. 7 for cutting member 240. Referring now to FIG. 8B, in at least one embodiment, the cutting member 240' may comprise a cutting surface 253' and a body including a distal body portion 255B' and a proximal body portion 255A'. The cutting surface 253' may be a part of and/or positioned on the distal body portion 255B'. The proximal body portion 255A' may define a cavity (not shown) and openings 248' communicating with the cavity. While not illustrated, the cavity may lie out of the plane define by the page of FIG. 8B and/or the longitudinal axis 225', for example. Additionally, each opening 248' may traverse the entire width of the cutting member's proximal body portion 255A', running from one side of the body portion 255A' to the other side. The cutting member 240' may also define a longitudinal axis 225' and the opening(s) 248' may define a plane that is parallel to the longitudinal axis 225'. In other words, the openings 248' may project to the sides of the cutting member 240'.

Focusing now on FIG. 8C, in at least one embodiment, the cutting member 240" may comprise a body 255" and a cutting surface 253" at a distal portion of the body 255". The body 255" may define a cavity 247" and openings 248" communicating with the cavity. Additionally, each opening 248" may traverse a side wall of the cutting member's body 255", running from a side of the body 255" to the cavity 247". The cutting member 240" may also define a longitudinal axis 225" and the opening(s) 248" may define a plane that is parallel to the longitudinal axis 225". In other words, the openings 248" may project to the sides of the cutting member 240". Further, arrows 287" illustrate a potential fluid flow path for a fluid flowing through the cutting member's cavity 247" and out openings 248", for example. Also, while not illustrated, cavity 247" may be offset from longitudinal axis 225".

Referring to FIG. 8D, in at least one embodiment, the cutting member 240'" may comprise a cutting surface 253'" and a body including a distal body portion 255B'" and a proximal body portion 255A'". The cutting surface 253'"

may be a part of and/or positioned on distal body portion 255B‴. The proximal body portion 255A‴ may define a cavity 247‴ and openings 248‴ communicating with the cavity 247‴. Further, the cutting member 240‴ may define a longitudinal axis 225‴ and the opening or openings 248‴ may define a plane that intersects the longitudinal axis 225‴. In other words, the openings may project proximally or distally with respect to the cutting surface 253‴ of the cutting member 240‴. As illustrated in FIG. 8D, the openings 248‴ project distally, towards the cutting surface 253‴. Further, arrows 287‴ illustrate a potential fluid flow path for a fluid flowing through the cutting member's cavity 247‴ and out openings 248‴, for example.

Additionally, as discussed above, a cutting member, such as cutting member 240‴, for example, may be configured to translate with respect to the first jaw 120A and/or second jaw 120B (see FIG. 4). In such embodiments, as discussed above with respect to cutting member 140, the cutting member 240‴ may be moved between a retracted position and a fully advanced position with respect to the first and/or second jaws 120A and/or 120B. However, unlike cutting member 140, the openings 248‴ of cutting member 240‴ may be positioned such that that the openings 248‴ are positioned proximal to one or both of energy delivery surfaces 175A and 175B when the cutting member 240‴ is at the fully advanced position. In other words, the opening(s) 248‴ may be positioned between the first jaw 120A and the handle 105 (FIGS. 1 and 2) when the cutting member is at the fully advanced position. In such embodiments, the cutting member openings 248‴ may not enter the space where tissue is being clamped, cut, and/or sealed, even when the cutting member 240‴ is fully advanced. Further, referring to FIG. 4, the first jaw's channel 142A may define a first length, L1. Referring to FIG. 8D, the cutting member 240‴ may define a second length, L2, as measured from one of the openings 248‴ to a distal edge of the cutting surface 253‴. In these embodiments, the first length may be approximately equal to the second length, or L1≈L2.

Figure 9:
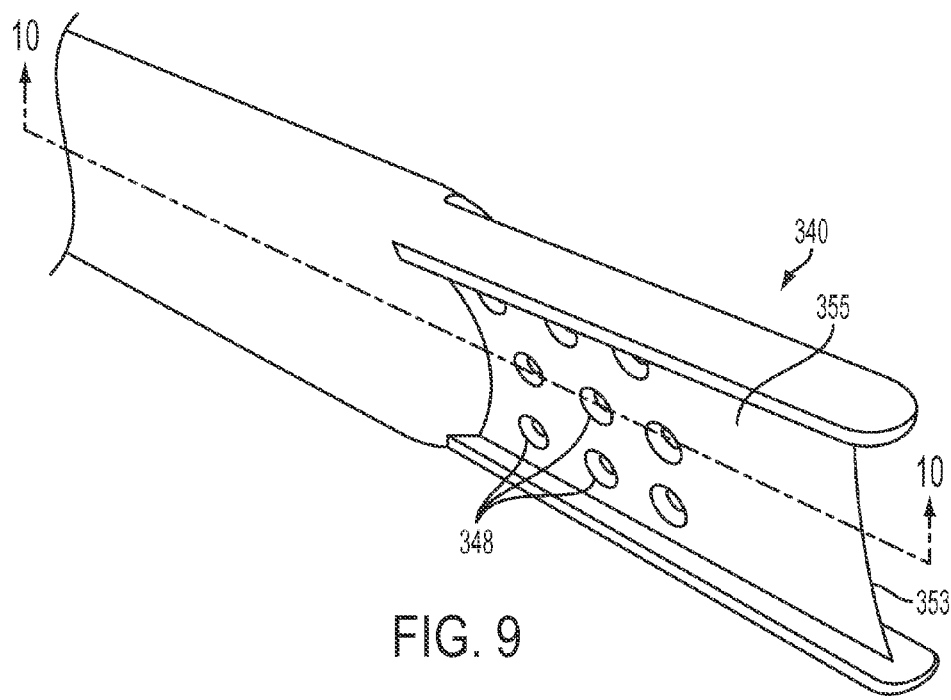
FIG. 9 is a perspective view of a portion of a cutting member of a surgical instrument according to a non-limiting embodiment.
Figure 10:
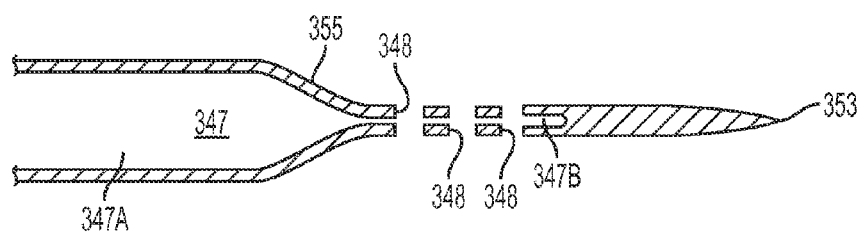
FIG. 10 is a cross-sectional view of the cutting member of FIG. 9, taken along line 10-10.

FIGS. 9-10 illustrate another exemplary embodiment of a cutting member 340, generally similar to cutting member 140 described above. For example, among other things, the cutting member 340 may comprise a body 355 and a cutting surface 353 at a distal portion of the body 355. The body 355 may define a cavity 347 and openings 348 communicating with the cavity 347. Additionally, each opening 348 may traverse a side wall of the cutting member's body 355, running from a side of the body 355 to the cavity 347. Additionally, the cavity 347 may comprise a larger portion 347A and a smaller portion 347B in fluid communication with each other. The smaller portion 347B may also directly communicate with the openings 348. Accordingly, the pressure of fluid flowing in or out of openings 348, from or through smaller cavity portion 347B may be increased over that provided to larger cavity portion 347A.

Figure 11:
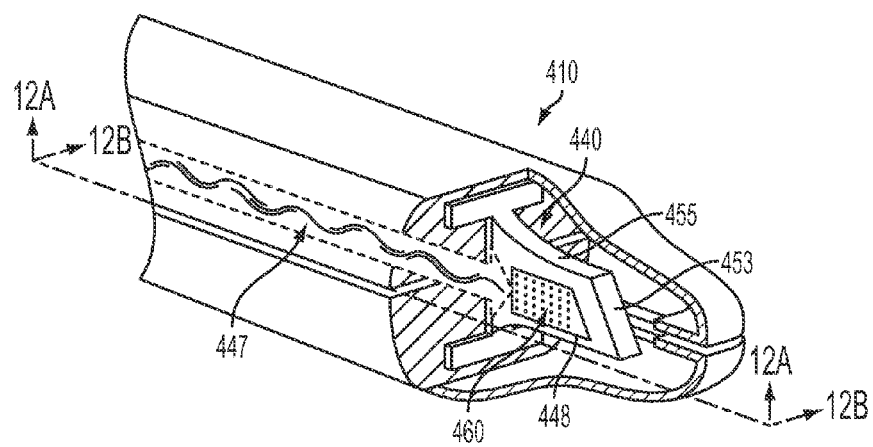
FIG. 11 is a perspective, partial-sectional view of a portion of an end effector of a surgical instrument according to a non-limiting embodiment.
Figure 12A:
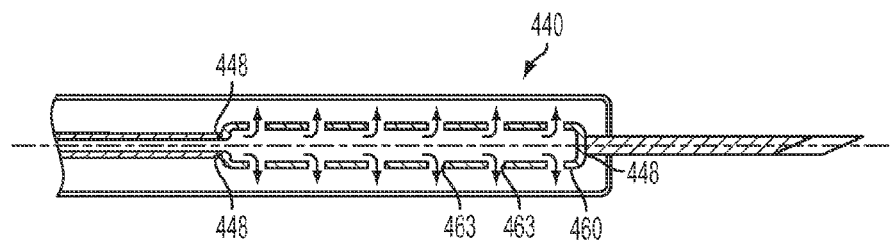
FIG. 12A is a partial cross-sectional view of a portion of a cutting member of the surgical instrument of FIG. 11, taken along line 12A-12A.
Figure 12B:
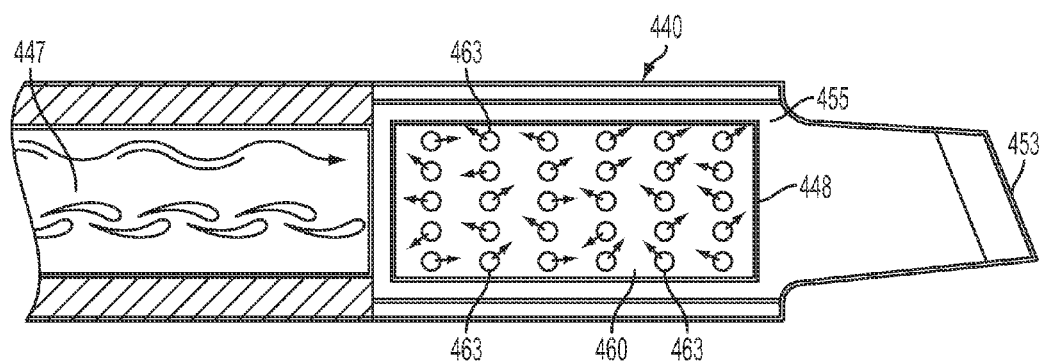
FIG. 12B is a partial cross-sectional view of a portion of a cutting member of the surgical instrument of FIG. 11, taken along line 12B-12B.

FIGS. 11-12B illustrate another exemplary embodiment of a cutting member 440, generally similar to cutting member 140 described above. As seen in FIG. 11, the cutting member 440 may be a part of an end effector 410, also similar to end effector 110 described above. In any event, among other things, the cutting member 440 may comprise a body 455 and a cutting surface 453 at a distal portion of the body 455. The body 455 may define a cavity 447 and at least one opening 448 communicating with the cavity 447. The opening 448 may be proximal to the cutting surface 453. Additionally, each opening 448 may traverse a side wall of the cutting member's body 455, running from a side of the body 455 to the cavity 447. Moreover, a porous material or insert 460 may be positioned within the opening 448. The porous insert 460 may comprise a cellular matrix and/or a sponge-like material. In any event, the porous insert may comprise one or more pores 463. The porous insert 460 and/or pores 463 may help direct any fluid passing therethrough in different directions as shown by the arrows in FIG. 12B.

Figure 13:
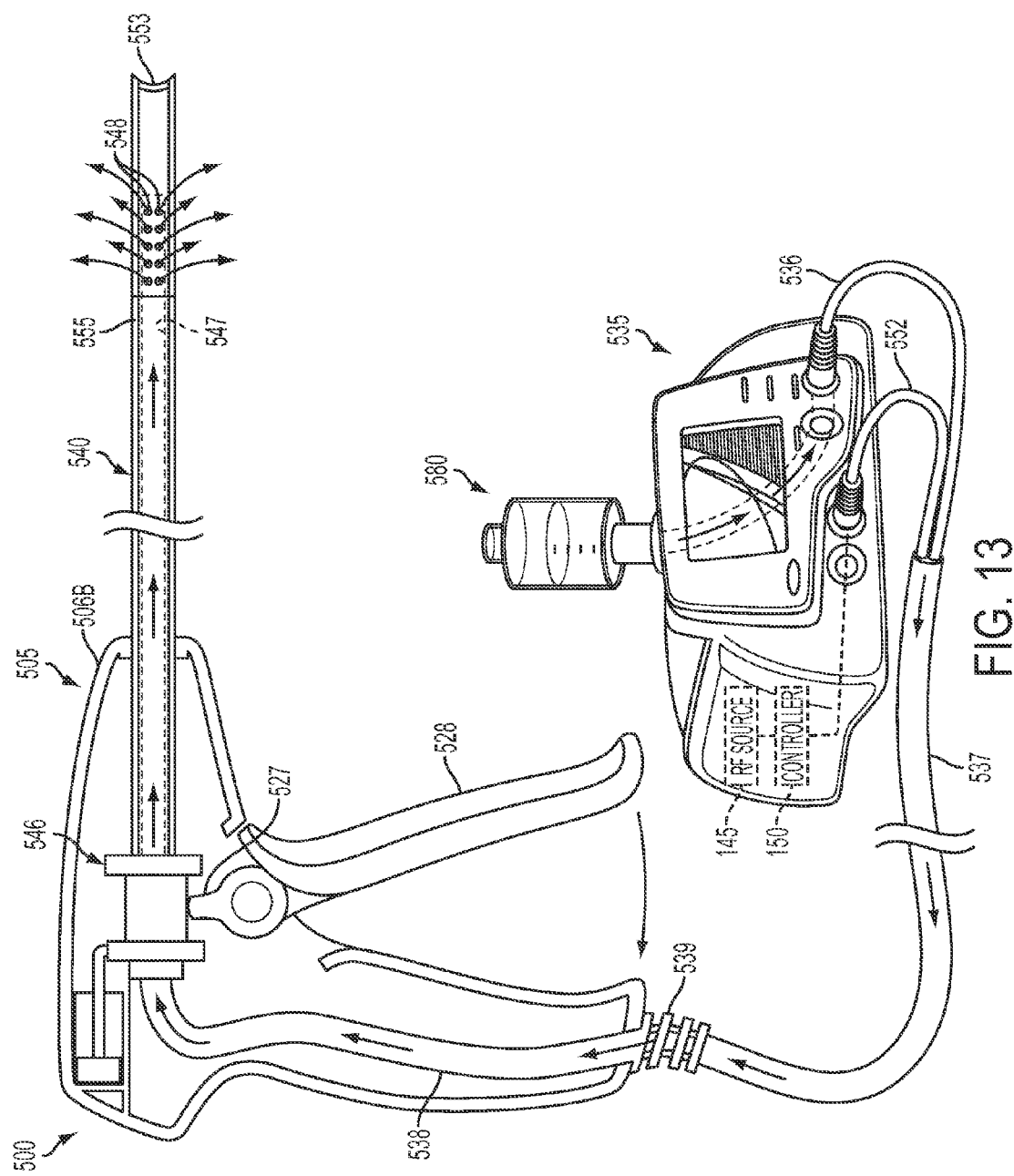
FIG. 13 is a side view of a surgical instrument according to a non-limiting embodiment; half of a handle body of the surgical instrument is removed to illustrate some of the components therein and some of the instrument's components are omitted for clarity.

Various mechanisms may be employed to move fluid through a cutting member in a surgical instrument. For example, referring now to FIG. 13, a surgical instrument 500 is shown coupled to a delivery unit 535. The surgical instrument 500 may be generally similar to surgical instrument 100 described above. For example, among other things, the surgical instrument 500 may comprise a handle 505 and a cutting member 540 operably coupled together. However, various components of the surgical instrument 500 are omitted for clarity. For instance, an elongate shaft operably coupled to the handle as well as additional components of an end effector operably coupled to the elongate shaft are not illustrated in FIG. 13.

In more detail, the surgical instrument 500 may comprise a trigger or lever arm 528 that may be movable with respect to a handle body 506B. Moving the arm 528 may correspondingly move an extension 527 formed on an upper portion of the arm 528, thereby causing a shuttle 546 to move in a proximal or distal direction. The shuttle 546 may be operably coupled to the cutting member 540. Accordingly, movement of the lever arm 528 may cause the cutting member 540 to translate with respect to the handle 505 and/or a jaw or jaws (not shown), for example.

The cutting member 540 may be coupled to a handle cable 538 either directly or via a passage in shuttle 546. In any event, the handle cable 538 may be coupled to a strain relief 539. Outside the handle 505, strain relief 539 may couple the handle tube 538 to a fluid cable 536 within an exterior cable 537. The exterior cable 537 may contain both the fluid cable 536 and a power cable 552, which both may be releasably coupled to the delivery unit 535.

The delivery unit 535 may comprise electrical source 145 and controller 150 electrically coupled to the power cable 552, as discussed above with respect to cable 152. Additionally, the delivery unit 535 may comprise a fluid chamber 580 holding water, distilled water, saline solution and/or any other suitable biocompatible fluid. The delivery unit 535 may further comprise a pump (not shown) configured to draw fluid out of the chamber 580 and deliver the fluid through the cables 536, 537, and 538 and into and through cutting member 540.

The cutting member 540 may comprise a body 555 and a cutting surface 553 at a distal portion of the body 555. The body 555 may define a cavity 547 and at least one opening 548 communicating with the cavity 547. The opening 548 may be proximal to the cutting surface 553. Accordingly, the fluid chamber 580 may be operably coupled to the cutting member cavity 547 such that the delivery unit 535 may move a fluid from chamber 580, to cutting member 540, and out openings 548, thereby cooling or dissipating heat from the cutting member 540, an end effector (not shown), and/or tissue.

In at least one embodiment, as discussed above, the fluid chamber 580 may be located outside the handle 505. However, in various embodiments, a fluid chamber may be located within a surgical instrument's handle. For example, referring now to FIG. 14, in at least one embodiment, a surgical instrument 600 may comprise a handle 605 containing a fluid chamber 680 therein. The surgical instrument 600 may be similar to surgical instrument 100 described above; however, various components of instrument 600 are omitted from FIG. 14 for clarity. For example, jaws of an end effector are not illustrated.

In more detail, the surgical instrument 600 may comprise a trigger or lever arm 628 that may be movable with respect to a handle body 606B. Moving the arm 628 may correspondingly move an extension (not shown) formed on an upper portion of the arm 628, thereby causing a shuttle 646 to move in a proximal or distal direction. The shuttle 646 may be operably coupled to the cutting member 640. Additionally, the chamber 680 may be fixedly connected to the handle body 606B and a piston or plunger 682 may be movably positioned within the chamber 680. The cutting member 640 may be coupled to the plunger 682 through a passage in shuttle 646. Accordingly, movement of the lever arm 628 may cause the cutting member 640 and/or plunger 682 to translate with respect to the handle body 606B, fluid chamber 680 and/or a jaw or jaws (not shown), for example.

Figure 14:
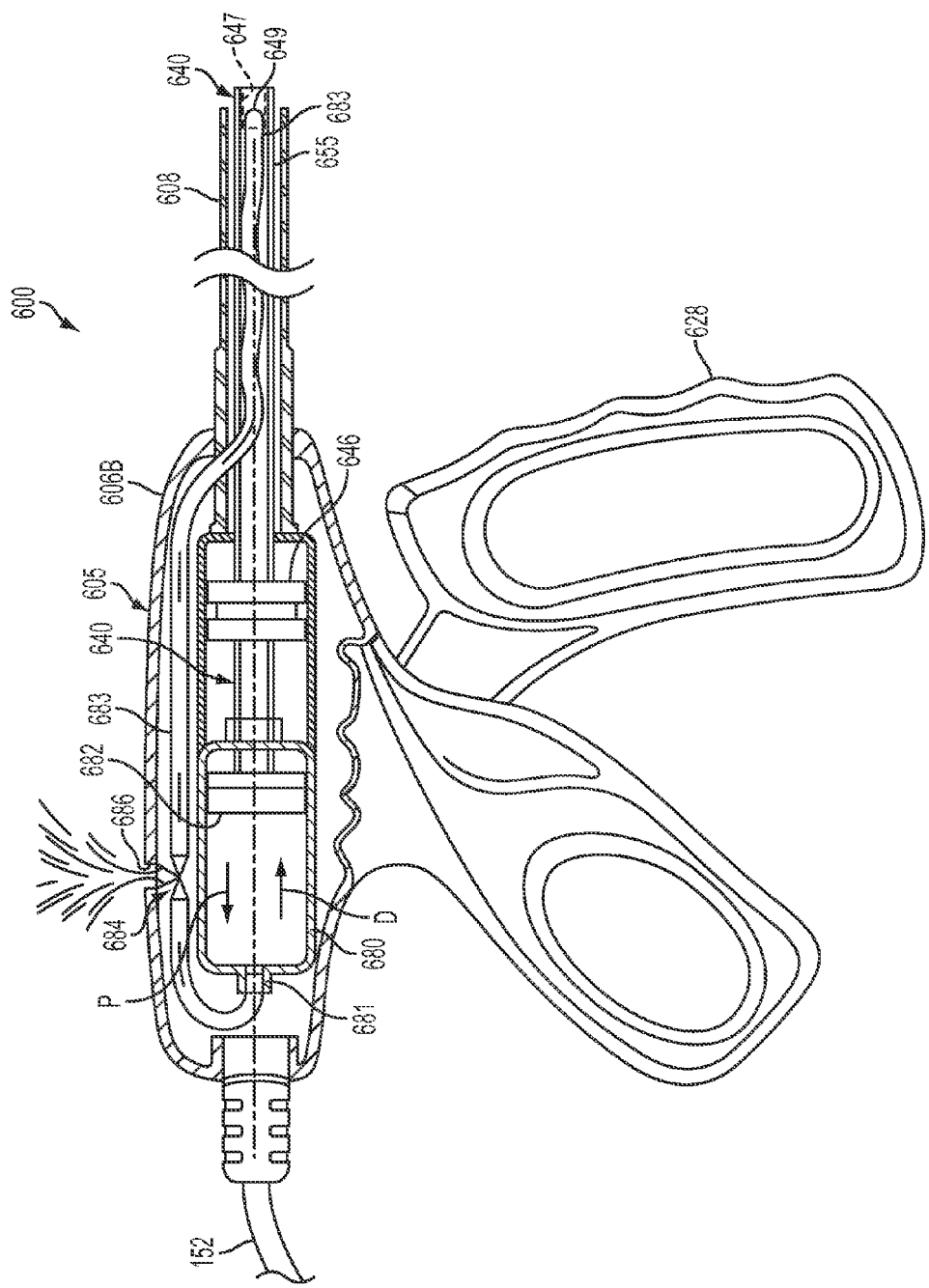
FIG. 14 is a side view of a handle of a surgical instrument according to a non-limiting embodiment; a portion of a handle body of the surgical instrument is cut away to illustrate some of the components therein.

Further, referring still to FIG. 14, the cutting member 640 may comprise a body 655 and a cutting surface (not shown) at a distal portion of the body 655. The body 655 may define a cavity 647 and at least one distal opening near the cutting surface communicating with the cavity 647. Further, the cavity 647 may be coupled to a tubing 683 at a proximal hole 649 formed in the body 655 of the cutting member, proximal to the distal opening or openings (not shown). The tubing 683 may traverse the elongate shaft 608 into the handle body 606B to ultimately connect to the fluid chamber 680 at a port 681. Accordingly, the fluid chamber 680 may be operably coupled to the cutting member cavity 647 such that a fluid may be moved from or to chamber 680, to or from cutting member 640, and out or in the opening(s), thereby cooling or dissipating heat from the cutting member 640, an end effector (not shown), and/or tissue.

In more detail, in various embodiments, the fluid chamber 680 may be configured to move or draw a fluid through the cutting member 640. For example, in at least one embodiment, the plunger 682 may be moved in a proximal direction, such as that designated by arrow "P," by operating the lever arm 628 such that the shuttle 646 causes the cutting member 640 and hence the plunger 682 to move in a proximal direction. In such embodiments, a fluid, comprising a gas and/or a liquid, such as carbon dioxide and/or saline solution, for example, may be forced out of the chamber 680 by the proximally moving plunger 682 and into and through the cutting member cavity 647 via tubing 683. Moreover, because the cutting member 640 and the plunger 682 are coupled together as shown, any cooling fluid may be driven out of the chamber 680 and through the cutting member 640 when the cutting member 640 is moved in a proximal direction. Thus, heat dissipation from a cooling fluid may be configured to occur after a cutting action is complete, when the cutting member 640 is returning to an initial, proximal position.

Alternatively, in at least one embodiment, the fluid chamber 680 may receive fluid drawn from an end effector, for example. In such embodiments, the plunger 682 may initially, before being actuated, be located at a proximal position within the chamber 680. The plunger 682 may then be moved in a distal direction, such as that designated by arrow "D," by operating the lever arm 628 such that the shuttle 646 causes the cutting member 640 and hence the plunger 682 to move in a distal direction, thereby creating a vacuum or lower pressure state within the fluid chamber 680. Such vacuum pressure may thereby cause a fluid, comprising gas, steam, water vapor, and/or liquid, for example, to be drawn into the cutting member cavity 647 via the distal openings near the cutting surface and/or end effector (not shown), for example. Thereafter, the drawn fluid may be forced into fluid chamber 680 through tubing 683.

In some embodiments, it may be desirable to evacuate fluid out of the surgical instrument 600. Accordingly, in at least one embodiment, referring still to FIG. 14, the surgical instrument 600 may further comprise a three-way valve 684 located inline with the tubing 683 and within the handle 605. In at least one embodiment, the valve 684 may comprise a bi-directional double check valve such as that manufactured by Value Plastics, Inc. of Fort Collins, Colo. In any event, two ports of the valve 684 may be coupled to different portions of the tubing 683 and one port of the valve 684 may be coupled to an exhaust 686 formed in the handle body 606B. The valve 684 may be configured to allow vacuum-pressure to be applied from the fluid chamber 684 to the cutting member cavity 647 through tubing 683. However, owing to the presence of the valve 684, fluid drawn from the end effector (not shown), through the cavity 647, and proximally through the tubing 683, may be diverted from the tubing 683 at valve 684 and expelled from the instrument 600 through the exhaust 686. Accordingly, in such embodiments, the surgical instrument 600 may be used multiple times since the fluid chamber 680 may not fill with fluid.

In various embodiments described herein, a fluid may be used to help dissipate heat from an end effector of a surgical instrument and/or tissue. In such embodiments, the fluid may comprise a liquid, such as distilled water and/or saline solution, for example. Further, in at least one embodiment, the liquid may be injected through a surgical instrument's jaws in a fashion similar to a steam iron. Accordingly, the target tissue may be kept hydrated during the sealing or welding process. Moisture in the tissue may help buffer the tissue such that the tissue's temperature remains at or around the temperature of the liquid, which may be boiling. Alternatively or additionally, the liquid may comprise nano-particles that are configured to absorb and store heat. In at least one embodiment, the nano-particles may be in suspension within a liquid, such as distilled water and/or saline solution, for example. The nano-particles may further help maintain tissue at a desired sealing temperature, for example, via a phase change of chemicals encapsulated in microspheres, for example. Further, in at least one embodiment, after the sealing process is complete, the nano-particles may be configured to (1) disperse through evaporation or out-gassing, for example, (2) biodegrade by breaking down and being absorbed and/or carried away by the patient's body, for example, and/or (3) remain inert and embedded in the tissue without compromising the strength of the tissue seal, for example.

Figure 15:
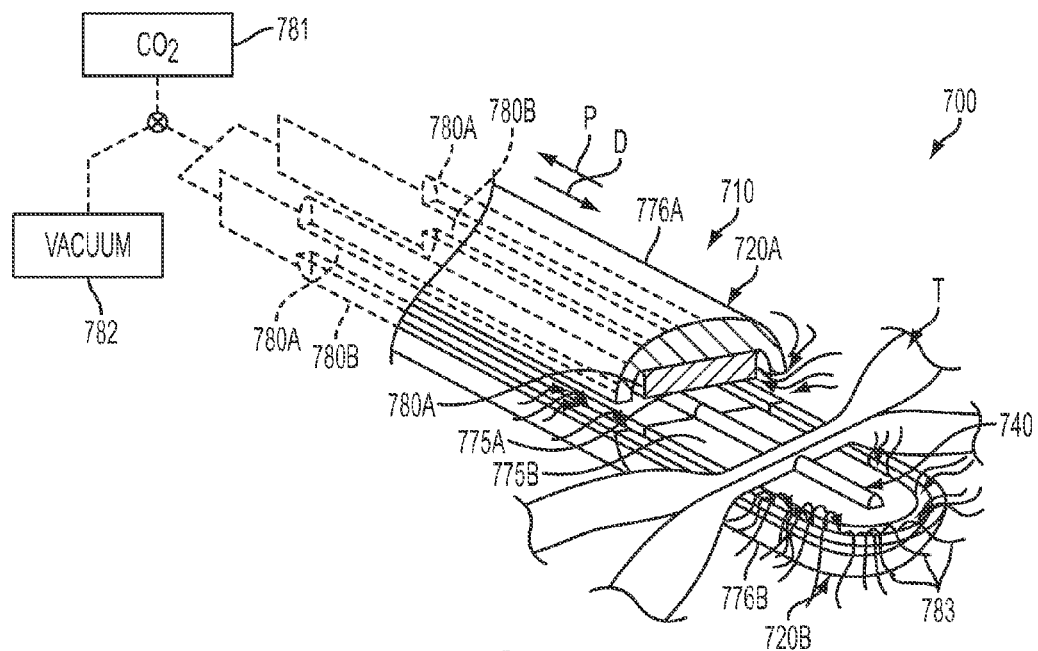
FIG. 15 is a perspective, partial-sectional view of a portion of an end effector of a surgical instrument according to a non-limiting embodiment.
Figure 16:
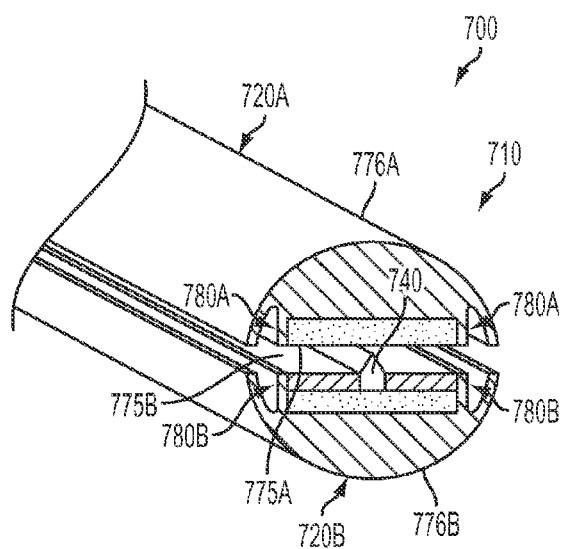
FIG. 16 is a perspective sectional view of a portion of the end effector of FIG. 15.

Additional embodiments of surgical instruments may dissipate heat generated within an end effector and/or tissue. For example, in various embodiments, referring to FIGS. 15 and 16, portions of an end effector 710 of a surgical instrument 700 are illustrated. The end effector 710 may be generally similar to end effector 110 described above. For example, among other things, the end effector 710 may comprise a first jaw 720A and a second jaw 720B operably coupled together and supporting a cutting member 740 therein. However, the cutting member 740 may be fixedly attached to one of the jaws 720A or 720B. Here, the cutting member 740 is shown fixed to second jaw 720B. Each jaw 720A, 720B may further comprise an energy delivery surface 775A and 775B and an exterior surface 776A and 776B, respectively. Accordingly, tissue "T" may be cut and sealed when the jaws 720A, 720B rotate from an open position (see FIG. 3) to a closed position (see FIG. 4) and energy is applied between surfaces 775A and 775B.

Either or both of the jaws 720A and 720B may further comprise open or exposed grooves 780A and 780B, respectively. The grooves 775A and 775B may be defined in the surfaces of the jaws 720A, 720B adjacent to energy delivery surfaces 775A and 775B. Further, the grooves 780A, 780B may each extend around the perimeter of the surfaces 775A, 775B, respectively. Moreover, each groove 780A and 780B may be positioned between an energy delivery surface 775A or 775B and an exterior surface 776A or 776B, within each respective jaw 720A and 720B.

In at least one embodiment, the grooves 780A, 780B may help evacuate heat and/or steam, for example, generated during energy delivery to the end effector 710. In such embodiments, the grooves 780A, 780B may be in fluid communication with a vacuum 782. The vacuum may help draw steam, water vapor, gas, liquid, or any other fluid, in directions generally designated by arrows 783 into the grooves 780A, 780B and into an elongate shaft (not shown) of the surgical instrument 700. Accordingly, such heated substances may escape the end effector 710 or tissue near the end effector 710.

Alternatively or additionally to the vacuum 782, the grooves 780A, 780B may be in fluid communication with a fluid source 781. The fluid source 781 may provide a gas, such as carbon dioxide, for example. In at least one embodiment, the fluid source may comprise an insufflation apparatus of a type typically used during a laparoscopic procedure, for example. The fluid source 781 may provide a continuous stream of gas to the grooves 780A, 780B such that the end effector 710 and/or tissue T may be cooled. As mentioned above, the fluid source 781 may provide a gas; however, in at least one embodiment, the fluid source may provide a liquid, such as a saline solution, for example. In such embodiments, the fluid source 781 may pump the liquid into the grooves 780A, 780B from an external reservoir, thereby continuously bathing the tissue T in a chilled or cooled medium. Also, in at least one embodiment, the fluid may comprise a gel or a two-part endothermic mixture, such as water mixed with potassium chloride, citric acid mixed with sodium bicarbonate, and/or ammonium chloride mixed with water, for example.

Figure 17:
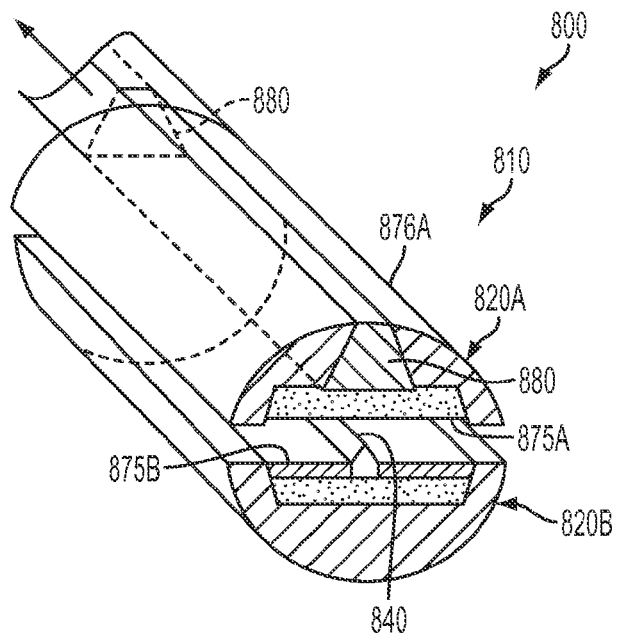
FIG. 17 is a perspective sectional view of a portion of an end effector of a surgical instrument according to a non-limiting embodiment.

In various embodiments, a surgical instrument may comprise a heat sink that may assist in dissipating heat from an end effector and/or tissue. For example, in at least one embodiment and referring to FIG. 17, a portion of an end effector 810 of a surgical instrument 800 is shown. The surgical instrument 800 may be generally similar to surgical instrument 700 described above. For example, among other things, the end effector 810 may comprise first and second jaws 820A and 820B that are operably coupled together. Each jaw 820A, 820B may comprise an energy delivery surface, such as energy delivery surfaces 875A and 875B, for example. A cutting member 840 may also be fixedly coupled to a jaw, such as jaw 820B, for example. However, the first jaw 820A may further comprise a heat sink, such as heat sink 880. In at least one embodiment, the heat sink 880 may be embedded in the first jaw 820A and may be exposed through an exterior surface 876A of the first jaw 820A. The heat sink 880 may comprise a heat conductive material, such as a metal, like aluminum, and/or a ceramic material, for example.

Figure 18:
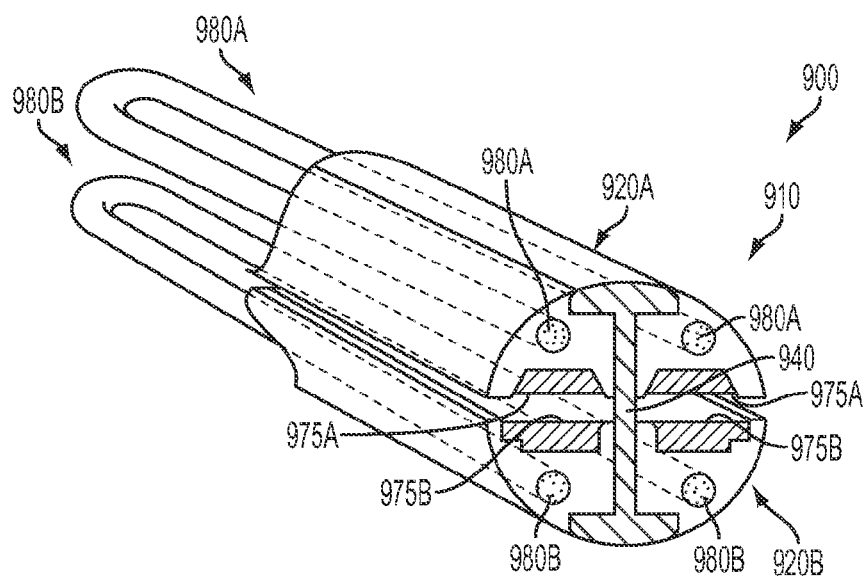
FIG. 18 is a perspective sectional view of a portion of an end effector of a surgical instrument according to a non-limiting embodiment.

In various embodiments, one or both of a surgical instrument's jaws may comprise a heat sink. For example, referring back to FIG. 16, the grooves 780A and/or 780B may contain and/or comprise a heat sink, which may comprise a heat conductive material, such as a metal, like aluminum, and/or a ceramic material, for example. Further, referring to FIG. 18, another embodiment of a portion of an end effector 910 of a surgical instrument 900 is shown. The surgical instrument 900 may be generally similar to surgical instrument 100 described above. For example, among other things, the end effector 910 may comprise a first jaw 920A and a second jaw 920B operably coupled together and movably supporting a cutting member 940. Each jaw 920A, 920B may also comprise an energy delivery surface 975A and 975B, respectively. However, the first jaw 920A may comprise a first heat sink 980A embedded therein and the second jaw 920B may comprise a second heat sink 980B embedded therein. Each heat sink 980A, 980B may be tubular in shape and extend to both sides of cutting member 940 such that heat may be effectively dissipated through the jaws 920A, 920B. Additionally, each heat sink 980A, 980B may comprise a heat conductive material, such as a metal, like aluminum, and/or a ceramic material, for example. In any event, in various embodiments including a heat sink, the heat sink may help efficiently transfer heat from tissue captured within an end effector's jaws away from the tissue and toward an elongate shaft of the surgical instrument, for example. In at least one embodiment, a heat sink may allow heat to equilibrate and/or dissipate throughout an extended length equal to or greater than the length of a jaw or jaws in contact with the tissue.

In various embodiments, a heat sink may comprise a Peltier device. Referring now to FIG. 19, a cross-sectional view of jaws 1220A and 1220B of an end effector 1210 of a surgical instrument 1200 are illustrated. The surgical instrument 1200 may be generally similar to the surgical instrument 100 described above. For example, among other things, the end effector 1200 may comprise the jaws 1220A and 1220B, which may be operably coupled together. Each jaw 1220A and 1220B may comprise an energy delivery surface 1275A and 1275B, respectively. Additionally, at least one jaw, for example, jaw 1220B may comprise at least one Peltier device, such as a first Peltier device 1281 and/or a second Peltier device 1282, either or both of which may be positioned adjacent to the energy delivery surface 1275B. A Peltier device may comprise a solid-state thermoelectric cooler. Additionally, a Peltier device may function on the principle that when a voltage differential is applied to a thermocouple-like device, a temperature differential may be created between two sides of the device.

In more detail, referring now to FIG. 20, each Peltier device, such as Peltier device 1281, for example, may comprise a first section 1281a and a second section 1281b. The sections 1281a and 1281b may have a voltage differential applied between them by a voltage source "V." As the voltage source V applies a voltage differential between the first section 1281a and the second section 1281b, heat energy may be moved from the first section 1281a to the second section 1281b.

Referring now to FIG. 21, a perspective sectional view of a portion of the jaw 1220B is shown. The Peltier devices 1281 and 1282 can be seen on the perimeter of the jaw 1220B, adjacent to the energy delivery surface 1275B. In at least one embodiment, the first section 1281a of the first Peltier device 1281 may be flush with the energy delivery surface 1275B and the second section 1281b may contact an interior surface of the jaw 1220B. Thus, when a voltage differential is applied to a Peltier device, such as Peltier device 1281, for example, heat may be moved from the first section 1281a to the second section 1281b and to the jaw 1220B, away from any tissue gripped by the jaw 1220B and/or energy delivery surface 1275B. Further, the Peltier device 1282 may be similar to the Peltier device 1281 described above. Additionally, the third and fourth Peltier devices 1283, 1285, may extend transversely from the first Peltier device 1281, and the fifth and sixth Peltier devices 1284, 1286 may extend transversely from the second Peltier device 1282. These transverse Peltier devices 1283, 1284, 1285, 1286 may further dissipate heat energy from tissue clamped between the jaws 1220A, 1220B (FIG. 19) and/or away from energy delivery surface 1275B, over that provided by longitudinal Peltier devices 1281 and/or 1282, to help prevent or resist undesired thermal alteration of tissue. In various embodiments, additional transverse Peltier devices and/or longitudinal Peltier devices may be added to the first jaw 1220A and/or the second jaw 1220B to provide additional heat dissipation. Additionally, in at least one embodiment, the Peltier devices may be instantly turned on and off at desired intervals and/or regulated in a linear fashion.

Figure 22:
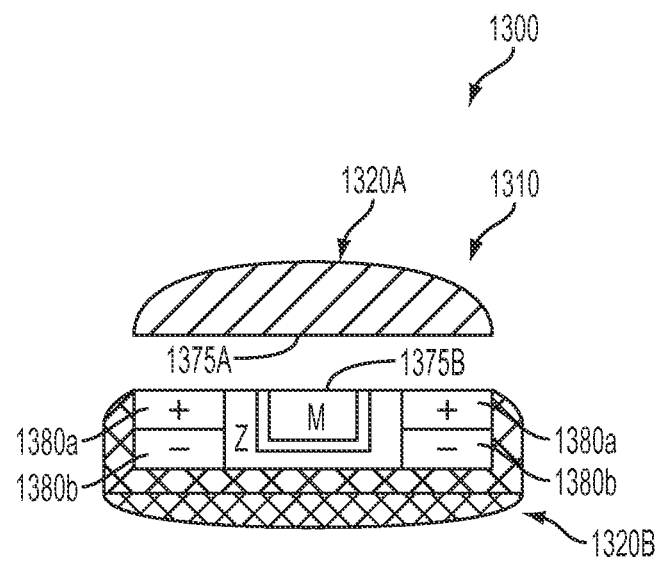
FIG. 22 is a cross-sectional view of an end effector of a surgical instrument according to a non-limiting embodiment.
Figure 23:
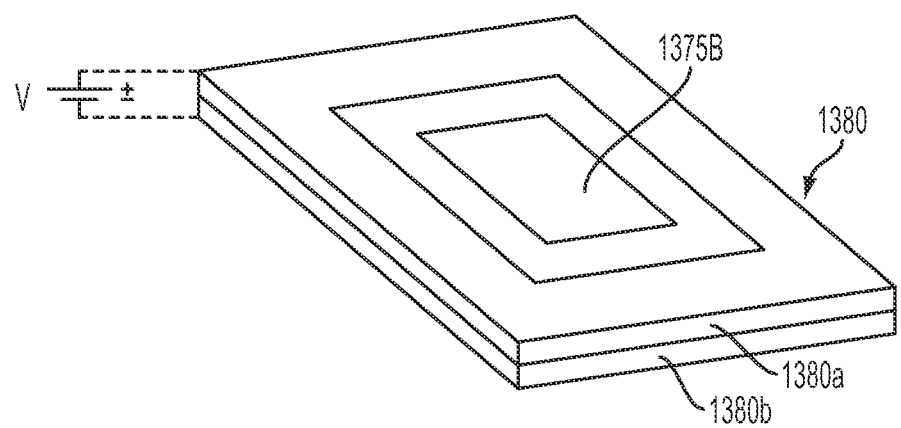
FIG. 23 is a perspective view of a portion of the end effector of FIG. 22.

FIGS. 22-23 illustrate an embodiment of another surgical instrument 1300 comprising an end effector 1310 and a Peltier device 1380. FIG. 22 is a cross-sectional view of the end effector 1310 and FIG. 23 is a perspective view of a portion of a jaw of the end effector 1310. In various embodiments, the surgical device 1300 may be generally similar to surgical device 100 described above in that the end effector 1310 may comprise two jaws 1320A and 1320B operably coupled together. However, the surgical device 1300 may function as a tissue spot welder and may not include a cutting member. The jaws 1320A and 1320B may comprise energy delivery surfaces 1375A and 1375B, respectively. Adjacent to and/or flush with the energy delivery surface 1375B may be the Peltier device 1380. The Peltier device 1380 may further extend around the entire perimeter of the energy delivery surface 1375B, to enhance the heat dissipation therefrom. Similar to Peltier device 1281 described above, Peltier device 1380 may comprise a first section 1380a and a second section 1380b. The sections 1380a and 1380b may be configured to receive a voltage differential between them from a voltage source "V." As the voltage source V applies a voltage differential between the first section 1380a and the second section 1380b, heat energy may be moved from the first section 1380a to the second section 1380b, thereby transferring and/or dissipating heat away from the energy delivery surface 1375B and/or tissue held between jaws 1320A and 1320B.

Figure 24:
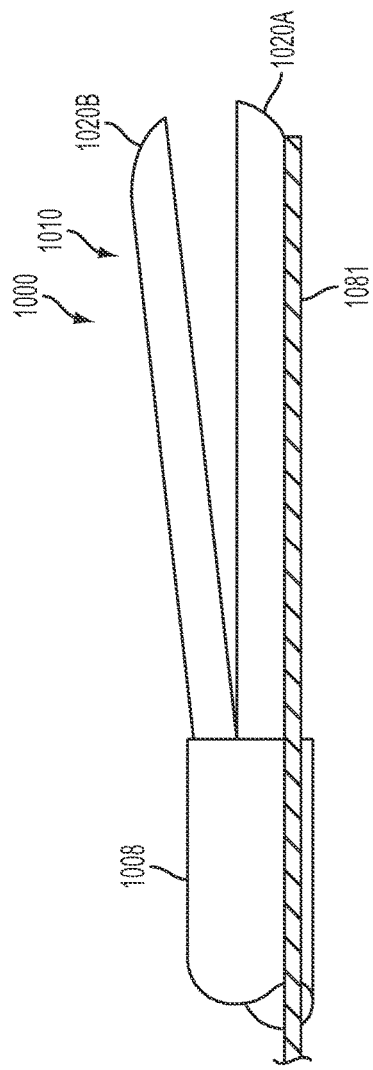
FIG. 24 is a side view of an end effector of a surgical instrument according to a non-limiting embodiment; the end effector is shown in an open configuration.

In various embodiments, heat dissipation from an end effector of a surgical instrument may be assisted by at least one heat pipe. In at least one embodiment, referring now to FIG. 24, the distal portion of a surgical instrument 1000 is shown. The surgical instrument 1000 may be generally similar to surgical instrument 100 described above. For example, among other things, the surgical instrument may comprise an end effector 1010 operably coupled to an elongate shaft 1008. The end effector 1010 may comprise a first jaw 1020A and a second jaw 1020B operably coupled together. The jaws 1020A and 1020B may be movable between an open configuration, such as that shown in FIG. 24, for example, and a closed configuration. Further, referring to FIG. 25, which shows a cross-sectional view of the end effector with the jaws 1020A and 1020B in a closed configuration, the end effector 1010 may comprise a cutting member 1040 that is configured to translate with respect to the jaws 1020A, 1020B. However, the end effector 1010 may also comprise at least one heat pipe, such as heat pipes 1081 and 1082. The heat pipes 1081, 1082 may be attached to the first jaw and extend proximally therefrom, through or next to elongate shaft 1008. Additionally, the heat pipes 1081, 1082 may be adjacent to the first jaw 1020A and may reside on opposing sides of the cutting member 1040.

Figure 26:
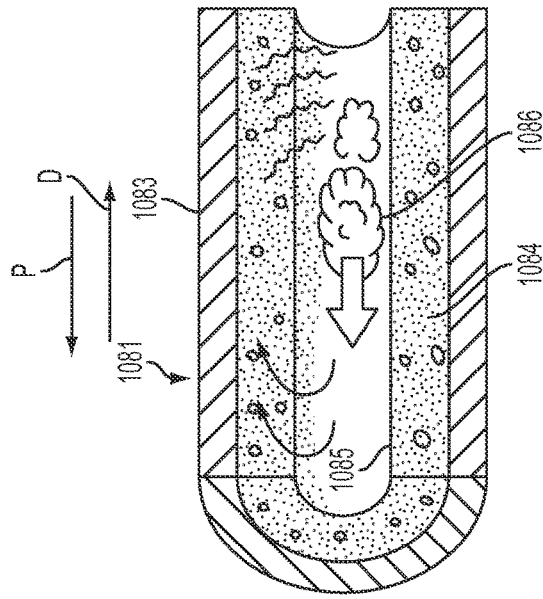
FIG. 26 is a perspective sectional view of a portion of a heat pipe of the surgical instrument of FIG. 24.
Figure 25:
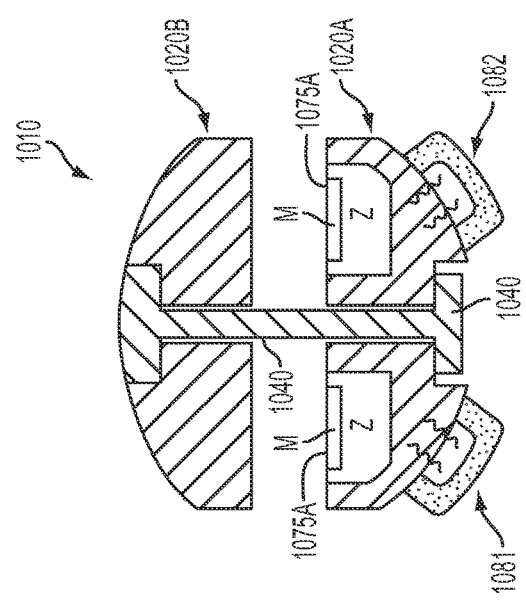
FIG. 25 is a cross-section view of the end effector of FIG. 24; the end effector is shown in a closed configuration.

In more detail, referring to FIG. 26, which shows a cross-sectional portion of the heat pipe 1081, the heat pipe 1081 may comprise an outer shell 1083 and an inner porous material 1084 defining an internal cavity 1085. The cavity 1085 may be sealed within the outer shell 1083 and may be partially evacuated and contain a heat transfer fluid 1086. As illustrated in FIG. 26, portions of the outer shell 1083 and the inner porous material 1084 have been cross-sectioned to show inner portions of the heat pipe 1081. In at least one embodiment, the outer shell 1083 of the heat pipe can be made of a thermally conductive and biocompatible metallic material positioned in direct contact with the jaw 1020A (FIG. 25). When the temperature of the jaw 1020A rises during energy delivery, as discussed above, the heat transfer fluid 1086 closest to the active jaw 1020A starts to evaporate, filling the internal cavity with vapor. The vapor condenses as it is forced proximally by a vapor pressure gradient, in a direction generally designated as "P," toward a proximal portion of the heat pipe 1081, which may be thermally connected to a heat sink, for example. The resulting liquid may then flow distally, in a direction generally designated as "D," via wicking properties associated with the inner porous material 1084. Accordingly, heat may be continuously carried away from the energized jaws 1020A, 1020B, in a proximal direction P, to decrease the working temperature between the jaws 1020A, 1020B. In various embodiments, the heat transfer fluid 1086 may be selected based on a desired working temperature. For example, the heat transfer fluid may comprise water and/or water-soluble (diluted) hydrocarbons. In at least one embodiment, the heat transfer fluid may comprise 30% ethanol and 70% water, for example. Additional details regarding an exemplary heat pipe or heat pipes may be found in U.S. Pat. No. 7,235,073, incorporated in its entirety by reference herein.

While the heat pipe(s) described above may be attached to one or both of the jaws, a heat pipe according to various embodiments may alternatively or additionally be attached to a cutting member. Accordingly, in at least one embodiment and referring now to FIG. 27, various portions of a surgical instrument 1100 are illustrated. The surgical instrument 1100 may be generally similar to surgical instrument 100 described above. For example, among other things, the surgical instrument may comprise an end effector 1110 and a handle 1105 operably coupled together by an elongate shaft 1108. The end effector 1110 may comprise a first jaw 1120A and a second jaw 1120B pivotably connected to each other. The end effector 1110 may further movably support a cutting member 1140 therein. In more detail, FIG. 28 depicts a partial side cross-sectional view of a portion of the surgical instrument 1100, taken along line 28-28 in FIG. 27, with the jaws 1120A and 1120B omitted for clarity. The cutting member 1140 may comprise a body 1155 and a cutting surface 1153 located at a distal portion of the body. Moreover, a heat pipe 1180 may be attached to the cutting member 1140. For example, in various embodiments, the heat pipe 1180 may be positioned within or attached to the exterior of the body 1155. Accordingly, in at least one embodiment, the heat pipe 1180 may be moved, relative to the jaws 1120A, 1120B, for example, when the cutting member 1140 is likewise moved. Also, in various embodiments, the heat pipe 1180 may extend along a portion of the body 1155. As illustrated in FIG. 28 and in at least one embodiment, the heat pipe 1180 may extend into the handle 1105, such that heat may be evacuated thereto. As illustrated in FIGS. 27-28, end portions of the heat pipe 1180 have been cross-sectioned to show inner portions of the heat pipe 1081; however it is to be understood that the heat pipe 1180 may be completely sealed at both ends. Further, in at least one embodiment, the heat pipe 1180 may be similar to the heat pipes 1081, 1082, described above.

In use and in at least one embodiment, referring to FIGS. 27 and 28, tissue "T" may be clamped between jaws 1120A, 1120B. Thereafter, the jaws 1120A, 1120B may be energized as described above with regard to surgical instrument 100, thereby creating a tissue weld "TW" in the tissue T. The cutting member 1140 may concurrently or thereafter be advanced through the tissue T, severing it. Additionally, as the cutting member 1140 is advanced, any heat built up in the end effector 1110, cutting member 1140, tissue T, and/or tissue weld TW, may be transported proximally via heat pipe 1180, thereby dissipating heat from the end effector 1110, cutting member 1140, tissue T, and/or tissue weld TW, for example.

Among other things, various heat dissipation means have been described above for dissipating heat from at least a portion of an end effector of a surgical instrument and/or tissue, for example. However, additional heat dissipation means, used independently, or in addition to one or more of the above described heat dissipation means, may also provide for enhanced heat dissipation of at least a portion of an end effector. Accordingly, in various embodiments, referring again to FIGS. 1 and 3, a surgical instrument, such as surgical instrument 100 seen in FIG. 1, may comprise an end effector 110 comprising at least one energy delivery surface, such as one or both energy delivery surfaces 175A and 175B seen in FIG. 3, and a heat dissipation means for dissipating heat from at least a portion of the end effector.

In at least one embodiment, the heat dissipation means may comprise a gas container. Referring now to FIG. 29, a surgical instrument 1400 may be generally similar to surgical instrument 100 described above. For example, among other things, the surgical instrument 1400 may comprise a handle 1405 and an elongate shaft 108 operably coupling the handle 1405 to the end effector 110 (FIG. 3). A gas container, such as gas container 1480, for example, may be operably coupled to the handle 1405. For example, as shown, the gas container 1480 may be fixedly attached to the handle inside the handle body 1406B. Alternatively, the gas container 1480 may be positioned outside the handle body 1406B. Further, the gas container 1480 may be configured to selectively release a gas such that the gas moves through the elongate shaft 108, in a distal direction, such as that demarcated by arrows 1486, and to at least a portion of the end effector 110 (FIG. 3), thereby dissipating heat from at least a portion of the end effector 110 and/or tissue.

In more detail, the gas container 1480 may include an outlet 1480B that is connected to a tubing 1483. The tubing 1483 may also be connected to a proximal hole 149 of a cutting member 140 as described above. The gas container 1480 may hold a compressed gas therein that may be released when a user presses a control button (not shown) that is configured to electrically and/or mechanically open outlet 1480B such that the compressed gas may escape the container 1480 into tubing 1483 and ultimately into the cutting member 140, for example. Alternatively, the outlet 1480B may be opened automatically before, during, and/or after activation of the energy deliver surfaces 175A, 175B (FIG. 3) via activation button 124. In various embodiments, the gas may be a biocompatible gas such as carbon dioxide, for example. When the compressed gas escapes to the environment outside the gas container 1480, the expanded gas may drop in temperature, thereby providing a cooled gas to the end effector 110 and/or tissue via the cutting member 140, as described above with respect to surgical instrument 100. Alternatively, in various embodiments, the gas may be routed internally through conduits enclosed within the jaws and/or electrodes, as a closed system, or externally such that the gas is piped to the sealing site and then released through orifices, such as openings 148 (FIG. 5) in the cutting member 140, to escape to the atmosphere, as an open system, or through a combination of the two routes. The flow of the gas out of the gas container 1480 may be initiated after sealing tissue, and in at least one embodiment, prior to opening the jaws 120A, 120B (FIG. 4) after sealing tissue, for example.

Figure 30:
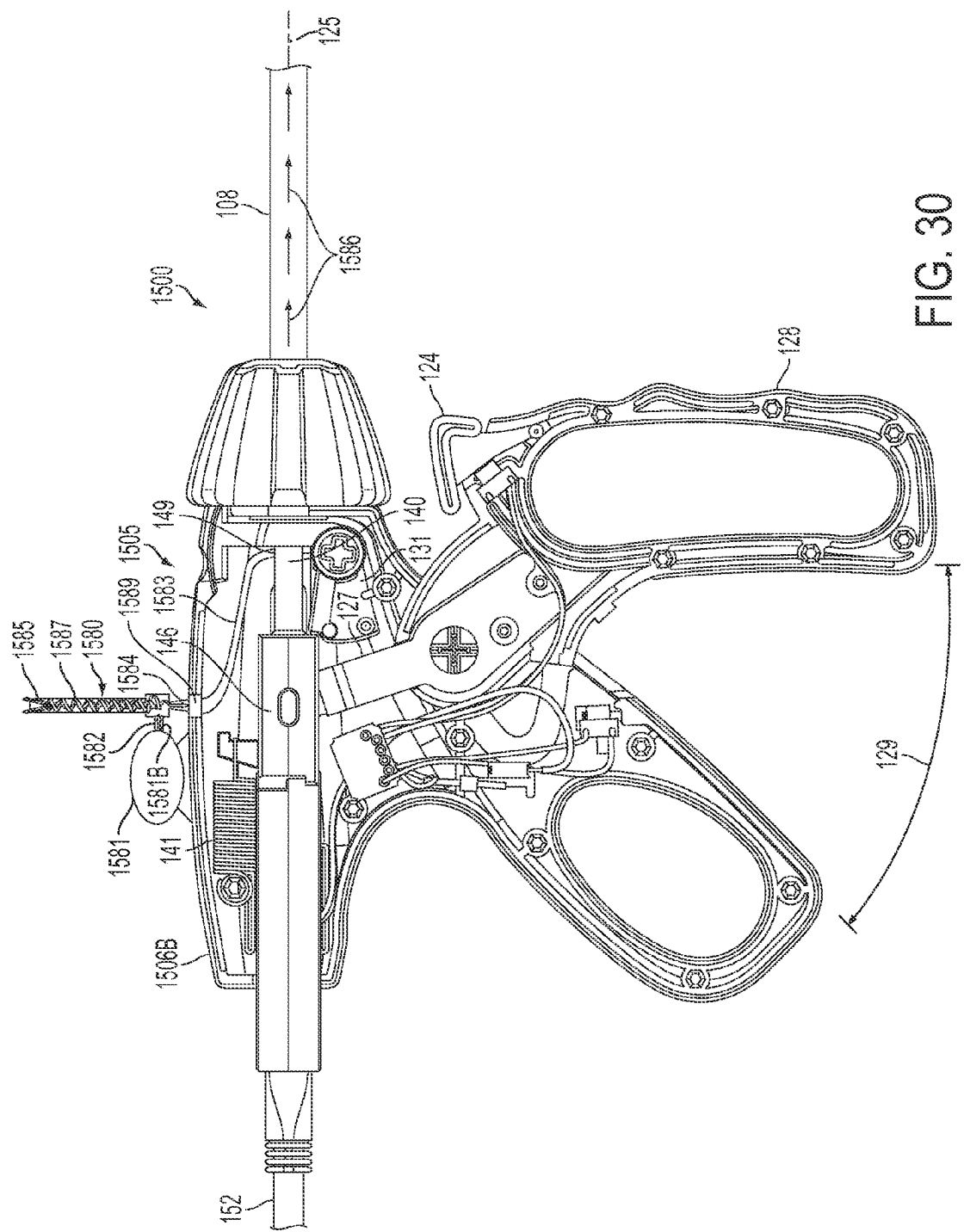
FIG. 30 is a side view of a handle of a surgical instrument according to a non-limiting embodiment; half of a handle body of the surgical instrument is removed to illustrate some of the components therein.

In at least one embodiment, the heat dissipation means may comprise a vortex tube. Referring now to FIG. 30, a surgical instrument 1500 may be generally similar to surgical instrument 100 described above. For example, among other things, the surgical instrument 1500 may comprise a handle 1505 and an elongate shaft 108 operably coupling the handle 1505 to the end effector 110 (FIG. 3). A vortex tube, such as vortex tube 1580, for example, may be operably coupled to the handle 1505. For example, as shown, the vortex tube 1580 may be fixedly attached to the handle 1505 outside the handle body 1506B. Alternatively, the vortex tube 1580 may be positioned inside the handle body 1506B. Further, the vortex tube 1580 may be configured to expel a cooled gas such that the gas moves through the elongate shaft 108, in a distal direction, such as that demarcated by arrows 1586, and to at least a portion of the end effector 110 (FIG. 3), thereby dissipating heat from at least a portion of the end effector 110 and/or tissue.

Figure 31:
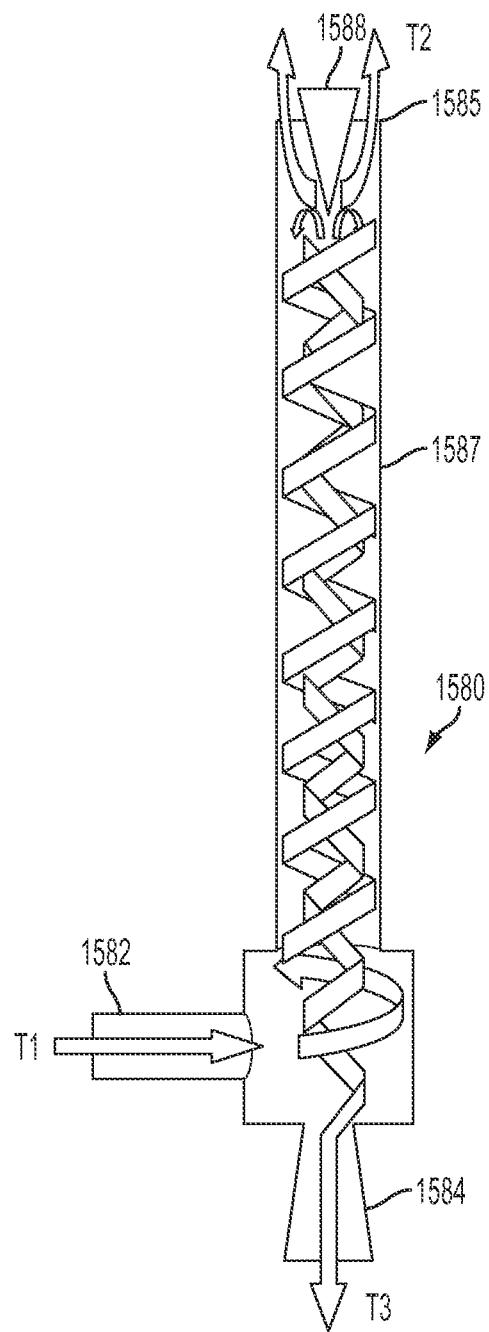
FIG. 31 is a schematic view of a vortex tube of the surgical instrument of FIG. 30.

In more detail, referring to both FIGS. 30 and 31, the vortex tube 1580 may comprise a body 1587 including an inlet 1582 and two outlets, warm exhaust or outlet 1585 and cool outlet 1584. The cool outlet 1584 may be connected to a port 1589 in the handle body 1505 that is connected to a tubing 1583. The tubing 1583 may also be connected to a proximal hole 149 of a cutting member 140 as described above. Additionally, the inlet 1582 may be connected to a gas container 1581 at a gas outlet 1581B. The gas container 1581 may be fixedly mounted to the handle body 1506B. The gas container may be generally similar to gas container 1480, described above. For example, among other things, the gas container 1581 may hold a compressed gas therein that may be released when a user presses a control button (not shown) that is configured to electrically and/or mechanically open outlet 1581B such that the compressed gas may escape the container 1581 into the vortex tube 1580 via inlet 1582. Also, alternatively, the outlet 1581B may be opened automatically before, during, and/or after activation of the energy deliver surfaces 175A, 175B (FIG. 3) via activation button 124. In various embodiments, the gas may be a biocompatible gas such as carbon dioxide, for example.

The vortex tube 1580 may be a Ranque-Hilsch vortex tube (manufactured by ExAir Corporation of Cincinnati, Ohio, for example) that is configured to create a cold and hot gas stream utilizing few or no moving parts, for example. Referring to FIG. 31, the vortex tube 1580 is shown in isolation from the other components of surgical instrument 1500. As illustrated, gas may enter the vortex tube via inlet 1582 at a first temperature T1. The gas may then travel in a helical manner within the body 1587 of the vortex tube 1580 toward warm outlet 1585. Upon nearing the warm outlet 1585, the moving gas may contact a conical nozzle 1588 that is sized and configured to cause warmer gas to be expelled through the warm outlet 1585, at a second temperature T2, and force cooler gas to be returned toward the cool outlet 1584. Upon reaching the cool outlet 1584, cooler gas may be expelled from the cool outlet 1584 at a third temperature T3. The third temperature T3 may be lower than the first and/or second temperatures T1 and T2, respectively. Accordingly, the vortex tube 1580 may create a cooler gas than that otherwise created from gas escaping the gas container 1581 without the assistance of the vortex tube 1580.

Referring again to FIG. 30, after gas is released into the vortex tube 1580 from the gas container 1581, a warm gas may be expelled from the warm outlet 1585 and a cooled gas may be expelled from the cool outlet 1584, as explained above. From the cool outlet 1584, gas may travel through the port 1589 and the tubing 1583, and into the cutting member 140 via proximal hole 149. Thereafter, gas may move through the cutting member 140 and/or elongate shaft 108 to at least a portion of the end effector 110 (FIG. 3), thereby dissipating heat therefrom, for example. In such embodiments, the cooled gas may be considered to be applied internally to the end effector 110, as the gas may be expelled from the cutting member 140 at distal openings, such as openings 148 (FIG. 5), for example. Alternatively, in at least one embodiment, the cooled gas may be applied externally to the jaws, via the elongate shaft 108, for example. Further, in at least one embodiment, cooled gas may be applied both internally and externally to the jaws. Additionally, while the vortex tube 1580 and/or gas container 1581 is shown directly attached to the handle body 1506B in FIG. 30, either or both the vortex tube and the gas container 1581 may be located in an auxiliary device, connected to the surgical device 1500 by a flexible tube, for example.

In at least one embodiment, the heat dissipation means may comprise an air cycle machine. In such embodiments, a surgical instrument (not shown) may be generally similar to instrument 100 described above. For example, the surgical instrument may comprise a handle and an elongate shaft operably coupling the handle to the end effector 110 (see FIG. 3). An air cycle machine may be operably coupled to the handle via a tube, for example. Further, the air cycle machine may be configured to expel a cooled gas such that the gas moves through the elongate shaft to at least a portion of the end effector 110 (FIG. 3), thereby dissipating heat from at least a portion of the end effector 110 and/or tissue. In such embodiments, the air cycle machine may be a miniaturized adaptation of an air cycle machine commonly used as a refrigeration unit on a turbine-powered aircraft. Accordingly, the air cycle machine may provide chilled gas, such as air, for example, to the end effector 110, jaws 120A, 120B (FIG. 3), and/or tissue. Briefly, the principle of operation of an air cycle machine is based upon the expansion of a compressed gas and may utilize an expansion turbine to extract work from the gas as it is being cooled. The turbine may concurrently run a compressor which may boost the compression of the gas upstream.

In at least one embodiment, the heat dissipation means may comprise room temperature distilled water circulated through the jaws of a surgical instrument in a single-pass fashion and/or released externally onto jaws of a surgical instrument and/or tissue at the completion of the sealing process. The surgical instrument of such an embodiment or embodiments may be generally similar to surgical instrument 100, described above. Further, such heat dissipation means may provide quick cooling of at least a portion of an end effector and/or tissue, for example.

In at least one embodiment, the heat dissipation means may comprise a closed-loop, refrigerant-based cooling system. Such a system may cool a surgical instrument's jaws following the completion of tissue sealing. The surgical instrument may be generally similar to surgical instrument 100, as described above. Additionally, the cooling system may include an evaporator coil that may be routed directly through the surgical instrument's jaws to provide efficient heat transfer.

In at least one embodiment, the heat dissipation means may comprise a cooled liquid created by a chemical function, such as a heat of solution and/or an endothermic chemical reaction, for example. The cooled liquid may be circulated through a surgical instrument's jaws immediately following the completion of tissue sealing by the instrument, for example. In such embodiments, the surgical instrument may be generally similar to surgical instrument 100, described above. In at least one embodiment, the cooled liquid may be created by mixing ammonium nitrate or potassium chlorate with water to produce a desired cooling effect.

In at least one embodiment, the heat dissipation means may comprise a magnetic refrigeration system. In such embodiments, a magnetic refrigeration system may be based on the magnetocaloric effect to provide cooling directly and/or indirectly, through, for example, a chilled working fluid, to a surgical instrument's jaws following the completion of tissue sealing by the instrument, for example. Such a system may utilize an alloy or alloys such as gadolinium-silicon-germanium ($Gd_5(Si_2Ge_2)$), for example. Additional information regarding such magnetic refrigeration may be found in the following article: Kerry Gibson, *Magnetic refrigerator successfully tested*, U.S. Department of Energy RESEARCH NEWS, at http://www.eurekalert.org/features/doe/2001-11/dl-mrs062802.php (Nov. 1, 2001).

In at least one embodiment, the heat dissipation means may comprise one or more thermoacoustic refrigeration devices. In such embodiments, at least one thermoacoustic device may rapidly cool a surgical instrument's jaws following the completion of tissue sealing by the instrument, for example. In such embodiments, the surgical instrument may be generally similar to surgical instrument 100, described above. In at least one embodiment, each thermoacoustic device may be a relatively small tubular device with few or no moving parts, which may use acoustic and/or ultrasonic energy to pump heat away from the surgical instrument's jaws. Additionally, the thermoacoustic devices may be cylindrical and/or are ring-shaped such that they have a recirculating configuration.

As noted above, the particular features, structures, or characteristics described herein may be combined in any suitable manner in one or more embodiments. Thus, the particular features, structures, or characteristics illustrated or described in connection with one embodiment may be combined, in whole or in part, with the features structures, or characteristics of one or more other embodiments without limitation. For example, at least one of the above embodiments describes a blade-based cooling mechanism and at least one embodiment describes a jaw-based cooling mechanism. In at least one embodiment, these mechanisms may be employed in a single instrument, for example.

The embodiments of the devices described herein may be introduced inside a patient using minimally invasive or open surgical techniques. In some instances it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted laparoscopically, such as in a multiple site laparoscopy, a single site laparoscopy, or a single incision laparoscopic surgery, for example. Further, the devices described here may be used in a a single port access procedure, for example. Additionally or alternatively, the devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Some portions of the devices may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small—keyhole—incision (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
    an end effector, comprising:
        a first jaw comprising a first channel;
        a second jaw operably coupled to the first jaw, wherein the second jaw comprises a second channel; and
        an electrode; and
    a moveable cutting member moveable between a retracted position and extended position, wherein the moveable cutting member is moveable through the first channel and the second channel when the first jaw and the second jaw are in a clamped configuration, and wherein the moveable cutting member comprises:
        a distal end comprising a cutting surface; and
        an intermediate portion proximal to the distal end, wherein the intermediate portion comprises an outer surface, wherein a cavity is defined in the intermediate portion, wherein at least one opening extends from the cavity to the outer surface, wherein the at least one opening is positioned intermediate the first jaw and the second jaw when the moveable cutting member is in the extended position, and wherein the at least one opening is configured to dissipate heat between the first jaw and the second jaw when the first jaw and the second jaw are in the clamped configuration.

2. The surgical instrument of claim 1, further comprising:
    an elongate shaft, wherein the end effector is operably coupled to the elongate shaft; and
    a handle operably coupled to the elongate shaft.

3. The surgical instrument of claim 1, further comprising a fluid chamber fluidly coupled to the cavity.

4. The surgical instrument of claim 3, wherein the fluid chamber contains at least one liquid, wherein the at least one liquid comprises nano-particles that are configured to absorb and store heat.

5. The surgical instrument of claim 1, further comprising a vacuum source fluidly coupled to the cavity.

6. The surgical instrument of claim 1, wherein a plurality of openings extend from the cavity to the outer surface, and wherein the plurality of openings are spaced apart along the intermediate portion.

7. The surgical instrument of claim 1, wherein the electrode comprises a U-shaped electrode positioned on the first jaw, and wherein a second electrode is positioned on the second jaw.

8. The surgical instrument of claim 7, further comprising a channel defined into the first jaw and at least partially around the U-shaped electrode.

9. The surgical instrument of claim 1, wherein the distal end comprises a closed distal end.

10. A surgical instrument, comprising:
   an end effector, comprising:
      a first jaw comprising a first channel;
      a second jaw operably coupled to the first jaw, wherein the second jaw comprises a second channel; and
      an electrode; and
   a moveable cutting member moveable between a retracted position and an extended position, wherein the moveable cutting member is moveable through the first channel and the second channel when the first jaw and the second jaw are in a clamped configuration, and wherein the moveable cutting member comprises:
      a distal cutting surface; and
      heat dissipation means for supplying fluid to tissue proximal to the distal cutting surface and clamped intermediate the first jaw and the second jaw, wherein the heat dissipation means does not extend past the electrode when the moveable cutting member is in the extended position.

11. The surgical instrument of claim 10, further comprising:
   an elongate shaft, wherein the end effector is operably coupled to the elongate shaft; and
   a handle operably coupled to the elongate shaft.

12. The surgical instrument of claim 10, further comprising a fluid chamber fluidly coupled to the heat dissipation means.

13. The surgical instrument of claim 12, wherein the fluid chamber contains at least one liquid, wherein the at least one liquid comprises nano-particles that are configured to absorb and store heat.

14. The surgical instrument of claim 10, wherein the moveable cutting member comprises a hollow portion.

15. A surgical instrument, comprising:
   an end effector, comprising:
      a first jaw comprising a first channel;
      a second jaw operably coupled to the first jaw, wherein the second jaw comprises a second channel; and
      an electrode; and
   a cutting member moveable between a retracted position and an extended position, wherein the moveable cutting member is moveable through the first channel and the second channel when the first jaw and the second jaw are in a clamped configuration, and wherein the cutting member comprises:
      an outer surface; and
      a fluid pathway, wherein the fluid pathway comprises at least one opening defined in the outer surface and a closed distal end, wherein the at least one opening is positioned intermediate the first jaw and the second jaw when the cutting member is in the extended position, and wherein the at least one opening is configured to dissipate heat between the first jaw and the second jaw when the first jaw and the second jaw are in the clamped configuration.

16. The surgical instrument of claim 15, wherein the cutting member is configured to translate between the first jaw and the second jaw along a longitudinal axis.

17. The surgical instrument of claim 15, further comprising:
   an elongate shaft, wherein the end effector is operably coupled to the elongate shaft;
   a handle operably coupled to the elongate shaft; and
   a fluid chamber fluidly coupled to the fluid pathway.

18. The surgical instrument of claim 17, further comprising a vacuum source fluidly coupled to the fluid chamber.

19. The surgical instrument of claim 15, wherein a plurality of openings are defined in the outer surface.

20. The surgical instrument of claim 15, wherein the outer surface comprises a cutting edge.

* * * * *